(12) United States Patent
Andersen et al.

(10) Patent No.: US 6,429,000 B1
(45) Date of Patent: *Aug. 6, 2002

(54) **PECTIN DEGRADING ENZYMES FROM *BACILLUS LICHENIFORMIS***

(75) Inventors: Lene Nonboe Andersen, Allerød; Martin Schülein, Copenhagen; Niels Erik Krebs Lange, Raleigh; Mads Eskelund Bjørnvad, Frederiksberg; Kirk Schnorr, Copenhagen, all of (DK)

(73) Assignee: Novozymes A/S, Begsvaard (DK)

( * ) Notice: Subject to any disclaimer, the term of this patent is extended or adjusted under 35 U.S.C. 154(b) by 104 days.

This patent is subject to a terminal disclaimer.

(21) Appl. No.: 09/670,141

(22) Filed: Sep. 26, 2000

Related U.S. Application Data

(63) Continuation of application No. 09/198,956, filed on Nov. 24, 1998, now Pat. No. 6,165,769, which is a continuation-in-part of application No. 09/073,684, filed on May 6, 1998, now Pat. No. 6,124,127.
(60) Provisional application No. 60/067,240, filed on Dec. 2, 1997.

Foreign Application Priority Data

Nov. 24, 1997 (DK) ............................................. 1344/97

(51) Int. Cl.$^7$ ............................. C12N 9/88; C07H 21/04
(52) U.S. Cl. .................... 435/232; 435/200; 435/252.3; 435/252.33; 435/320.1; 536/23.2; 536/23.7
(58) Field of Search ............................. 435/232, 252.3, 435/252.31, 252.33, 320.1, 200; 536/23.2, 23.7

(56) References Cited

FOREIGN PATENT DOCUMENTS

| EP | 0 683 228 A2 | 11/1995 |
| EP | 0 870 834 A1 | 10/1998 |
| WO | WO 98/45393 | 10/1998 |

OTHER PUBLICATIONS

Abstract Derwent Accession No. 81–54142D [25] JP 56068393.
Nasser et al., (1990) Biochimie 72:689–695.
Karbassi et al., (1980) Can. J. Microbiol. 26:377–384.
Kelly et al., (1978) Can. J. Microbiol. 24:1164–1172.
Godfrey et al., (1994) J. of Applied Bacteriology 76:13–21.
Yoshimitzu Miyazaki (1991) Agric. Biol. Chem. 55(1):25–30.
Sakamoto et al., (1996) FEBS Letters 398:269–273.
STN International, Chem. Abst. 118:250320.
Derwent Accession No. 88–209811.
EMBL, Database Genbank/DDBJ, Accession No. L416731.
EMBL, GenBank/DDJ Accession No. D83791.

*Primary Examiner*—Nashaat T. Nashed
(74) *Attorney, Agent, or Firm*—Elias Lambiris

(57) ABSTRACT

Pectin degrading enzymes derived from or endogeneous to *Bacillus licheniformis* or other Bacillus species which are at least 99% homologous to *Bacillus licheniformis* based on aligned 16S rDNA sequences have optimum activity at pH higher than 8. The pectin degrading enzymes belongs to the enzyme classes pectate lyases (EC 4.2.2.2), pectin lyases (EC 4.2.2.10) and polygalacturonases (EC 3.2.1.15) and are useful in industrial processes under alkaline conditions such as in textile processing and as an active ingredient eg in laundry detergents and hard surface cleaning products.

8 Claims, No Drawings

SEQUENCE LISTING

<160> NUMBER OF SEQ ID NOS: 26

<210> SEQ ID NO 1
<211> LENGTH: 1485
<212> TYPE: DNA
<213> ORGANISM: Bacillus licheniformis

<400> SEQUENCE: 1

```
atgaaactga tcaaaaacgc atcttttatc atttcttttt tggctgcggc cggcatttat      60
tttttattag gtacagtcgc tgcttctgcg gcaaacgaag attatccgga acagatgatc     120
aggctggaaa gctcatcagg cttaaatatt acgcccgccg ggaatcaaga caacgcaccg     180
ttaacagcaa aacagacgag cggagaaaaa gaagaaagat ggaggcttga tacgtctgac     240
ggcaaacaat tcaaaatcag aaatatggat agcggcaaaa ttatcatccc tgcccattac     300
gcactgtcag acaataatcc ggctgtggtc tactatgaca attcacggaa ggaagagttg     360
tggaatatca tcggggccga caaagacgga aacggagatt ttatcacgta taaaatcgtc     420
```

-continued

```
agtgcacaaa acagcagcct tgcactgaca ctggacggca gcggagtgaa gcttgccaaa      480
tatacgggca gctccgtcca aaagtggaag cttccaagcg acgggctcga aggtttcgca      540
ggctatgcaa gggaaacgaa cggcaagcag aaaacaggca caaccggcgg cctgcttgga      600
aaagtcgtct atgtcaataa tctgggcgaa ctgaaggcca atattgaaga ttcaacgccg      660
cgcacgattg tcgtctccag caatatcggc gcttcagcca aacggtatt aacggtgggc       720 gccaataaaa caatcatcgg ctcgtatgaa aaacataagc tgaataacat ttactttaaa      780
acaaaagcgg actctggcaa cgttattttc aaaaatctgg tcattgcaca tgatgcatcc      840
ataaatgaaa acaatgacat ccctgtttac attaccgatt cgagaaacta ctggattgac      900
catgtcacat tccaaggcca cagctatacg gcaaacggcc acgatctcga caagctctta      960
tacgtcggcg ctaaagccga ttacgtcaca ctgtcgcaca gcacattcac agaccacagg     1020
tacggcctga ttctcggctg gcctcaagat gacaagcaat accacagtat atataatggc     1080
tatccgcgga tgacaatcag ccacaatcgc tttgagaatc tctatgtcag ggcgcccggg     1140
ttgatgcgtt acggctatta tcacgtgaaa agcaattata tcaacaatta ccaccttggc     1200
ttcacgatta cgacattggc gaaaatatat tctgaagcca attacttcgg cacgggcaat     1260
gagaaaggca tactggatga ttacggagac ggcgcgttta agatgtcgg gtcatatccg      1320 gcgataaagg ggcagaaatc gcctgagaca agctggacac cttcatccaa ctacagctat     1380
cggacgatga aggccggcaa tgccaaagct tttgccaaac ggtacgcagg tgcgcagcgc     1440
accgctctgt actatgcgaa ttacagccag tttaaaaaag actaa                    1485
```

```
<210> SEQ ID NO 2
<211> LENGTH: 494
<212> TYPE: PRT
<213> ORGANISM: Bacillus licheniformis

<400> SEQUENCE: 2
```

Met Lys Leu Ile Lys Asn Ala Ser Phe Ile Ile Ser Phe Leu Ala Ala
1               5                   10                  15

Ala Gly Ile Tyr Phe Leu Leu Gly Thr Val Ala Ala Ser Ala Ala Asn
            20                  25                  30

Glu Asp Tyr Pro Glu Gln Met Ile Arg Leu Glu Ser Ser Ser Gly Leu
        35                  40                  45

Asn Ile Thr Pro Ala Gly Asn Gln Asp Asn Ala Pro Leu Thr Ala Lys
    50                  55                  60

Gln Thr Ser Gly Glu Lys Glu Glu Arg Trp Arg Leu Asp Thr Ser Asp
65                  70                  75                  80

Gly Lys Gln Phe Lys Ile Arg Asn Met Asp Ser Gly Lys Ile Ile Ile
                85                  90                  95

Pro Ala His Tyr Ala Leu Ser Asn Asn Pro Ala Val Val Tyr Tyr
            100                 105                 110

Asp Asn Ser Arg Lys Glu Glu Leu Trp Asn Ile Ile Gly Ala Asp Lys
        115                 120                 125

Asp Gly Asn Gly Asp Phe Ile Thr Tyr Lys Ile Val Ser Ala Gln Asn
    130                 135                 140

Ser Ser Leu Ala Leu Thr Leu Asp Gly Ser Gly Val Lys Leu Ala Lys
145                 150                 155                 160

Tyr Thr Gly Ser Ser Val Gln Lys Trp Lys Leu Pro Ser Asp Gly Leu
                165                 170                 175

Glu Gly Phe Ala Gly Tyr Ala Arg Glu Thr Asn Gly Lys Gln Lys Thr

```
                    180              185              190
Gly Thr Thr Gly Gly Leu Leu Gly Lys Val Val Tyr Val Asn Asn Leu
            195              200              205
Gly Glu Leu Lys Ala Asn Ile Glu Asp Ser Thr Pro Arg Thr Ile Val
    210              215              220
Val Ser Ser Asn Ile Gly Ala Ser Ala Lys Thr Val Leu Thr Val Gly
225              230              235              240
Ala Asn Lys Thr Ile Ile Gly Ser Tyr Glu Lys His Lys Leu Asn Asn
                245              250              255
Ile Tyr Phe Lys Thr Lys Ala Asp Ser Gly Asn Val Ile Phe Lys Asn
            260              265              270
Leu Val Ile Ala His Asp Ala Ser Ile Asn Glu Asn Asn Asp Ile Pro
    275              280              285
Val Tyr Ile Thr Asp Ser Arg Asn Tyr Trp Ile Asp His Val Thr Phe
    290              295              300
Gln Gly His Ser Tyr Thr Ala Asn Gly His Asp Leu Asp Lys Leu Leu
305              310              315              320
Tyr Val Gly Ala Lys Ala Asp Tyr Val Thr Leu Ser His Ser Thr Phe
                325              330              335
Thr Asp His Arg Tyr Gly Leu Ile Leu Gly Trp Pro Gln Asp Asp Lys
            340              345              350
Gln Tyr His Ser Ile Tyr Asn Gly Tyr Pro Arg Met Thr Ile Ser His
            355              360              365
Asn Arg Phe Glu Asn Leu Tyr Val Arg Ala Pro Gly Leu Met Arg Tyr
    370              375              380
Gly Tyr Tyr His Val Lys Ser Asn Tyr Ile Asn Asn Tyr His Leu Gly
385              390              395              400
Phe Thr Ile Thr Thr Leu Ala Lys Ile Tyr Ser Glu Ala Asn Tyr Phe
                405              410              415
Gly Thr Gly Asn Glu Lys Gly Ile Leu Asp Asp Tyr Gly Asp Gly Ala
            420              425              430
Phe Lys Asp Val Gly Ser Tyr Pro Ala Ile Lys Gly Gln Lys Ser Pro
            435              440              445
Glu Thr Ser Trp Thr Pro Ser Ser Asn Tyr Ser Tyr Arg Thr Met Lys
    450              455              460
Ala Gly Asn Ala Lys Ala Phe Ala Lys Arg Tyr Ala Gly Ala Gln Arg
465              470              475              480
Thr Ala Leu Tyr Tyr Ala Asn Tyr Ser Gln Phe Lys Lys Asp
                485              490
```

<210> SEQ ID NO 3
<211> LENGTH: 666
<212> TYPE: DNA
<213> ORGANISM: Bacillus licheniformis

<400> SEQUENCE: 3

```
atgaagagat tagcaggtac ggttattttg tcaggtttgc tcgtatgcgg gtttggacag      60
gctctgcctg aaaaagcttt ggccgccgag gtcgttcaca aaacgatcgt agtcgagaaa     120
ggccaaacgt atgacggaaa aggcaagcgg ctgattgcag tccggagct cggggacggc     180
agccaacgcg aggatcaaaa accgattttc aaagtggagg atggtgcaac gctcaaaaat     240
gtcgtgcttg cgctcctgc tgctgatggt gttcacacat atgaaacgc ttccataaac     300
aacgttgttt gggaagatgt cggcgaagat gccttgactg tcaaaagcga aggaagtgtc     360
```

-continued

```
acgataaacg gaggatcggc ccggcttgcc gcggacaaaa tctttcagat taataaagcg      420
agcacattta ccgtgaaaaa ttttactgcc gatcaaggag gcaaattcat tcgccagctc      480
ggaggctcga catttaaagc cgtggtcaat attgataact gtacgattac aaacatgaaa      540
gaggcgatct tccgaaccga cagcagtaca agttccgtta caatgacaaa tacaagatac      600
tcaaaagtcg gtcagaaatg gatcggtgtg aagcatgcta cggaaagaaa caatcatgaa      660
ttttaa                                                                 666
```

<210> SEQ ID NO 4
<211> LENGTH: 221
<212> TYPE: PRT
<213> ORGANISM: Bacillus licheniformis
<400> SEQUENCE: 4

```
Met Lys Arg Leu Ala Gly Thr Val Ile Leu Ser Gly Leu Leu Val Cys
 1               5                  10                  15

Gly Phe Gly Gln Ala Leu Pro Glu Lys Ala Leu Ala Ala Glu Val Val
                20                  25                  30

His Lys Thr Ile Val Val Glu Lys Gly Gln Thr Tyr Asp Gly Lys Gly
            35                  40                  45

Lys Arg Leu Ile Ala Gly Pro Glu Leu Gly Asp Gly Ser Gln Arg Glu
    50                  55                  60

Asp Gln Lys Pro Ile Phe Lys Val Glu Asp Gly Ala Thr Leu Lys Asn
65                  70                  75                  80

Val Val Leu Gly Ala Pro Ala Ala Asp Gly Val His Thr Tyr Gly Asn
                85                  90                  95

Ala Ser Ile Asn Asn Val Val Trp Glu Asp Val Gly Glu Asp Ala Leu
            100                 105                 110

Thr Val Lys Ser Glu Gly Ser Val Thr Ile Asn Gly Gly Ser Ala Arg
        115                 120                 125

Leu Ala Ala Asp Lys Ile Phe Gln Ile Asn Lys Ala Ser Thr Phe Thr
    130                 135                 140

Val Lys Asn Phe Thr Ala Asp Gln Gly Gly Lys Phe Ile Arg Gln Leu
145                 150                 155                 160

Gly Gly Ser Thr Phe Lys Ala Val Val Asn Ile Asp Asn Cys Thr Ile
                165                 170                 175

Thr Asn Met Lys Glu Ala Ile Phe Arg Thr Asp Ser Ser Thr Ser Ser
            180                 185                 190

Val Thr Met Thr Asn Thr Arg Tyr Ser Lys Val Gly Gln Lys Trp Ile
        195                 200                 205

Gly Val Lys His Ala Thr Glu Arg Asn Asn His Glu Phe
    210                 215                 220
```

<210> SEQ ID NO 5
<211> LENGTH: 1248
<212> TYPE: DNA
<213> ORGANISM: Bacillus licheniformis
<400> SEQUENCE: 5

```
ttgcgatatt taaaacaggc gtcacattat aaagggagcg gtaacgtgag tctacagaaa       60
ataaaacaag agattgtaaa gaagctgaag gttccggtat ttccgaatcg ctcatttgat      120
gtcacatcgt ttggggctga cgaaaacgga aaaaacgatt cgaccgaagc gatacagaag      180
gcgattgatc aagcccacca agccggcggc ggaagagtaa cggttcctga aggcgtgttt      240
ctttccggtg cgctcagatt gaaaagcaat gtggatcttc atattgcaaa gggagcggtg      300
```

-continued

```
atcaaattca gtcagaaccc tgaagattat ctccctgttg tgctgacgag gtttgaagga      360
gtcgagctct ataattattc accgctcatc tacgcttacg aagccgataa tattgcgata      420
accggaaagg gcacgcttga cggtcaagga gatgacgagc attggtggcc gtggaaaaga      480
ggaacgaacg gccagccttc acaggaaaaa gatcggaacg ctttgtttga atggctgag       540 cgcggtatcc cggtcactga gcggcagttt ggaaaagggc attatttgcg gccgaatttc      600
attcagccgt atcgctgcaa acatatattg attcaaggcg tcactgtgct gaattcgccg      660
atgtggcaag ttcatcccgt gctttgcgag aatgtgacag tggacggcat caaagtcatc      720
ggacacggcc ccaataccga cggagtcaac ccggaatcgt gtaaaaacgt ggtgatcaag      780
ggctgccatt ttgataatgg agacgactgc atcgccgtca atcgggaag aaatgcggac       840 ggccgaagga tcaacattcc gtcggaaaac atcgtcattg aacataacga aatgaaagac      900
gggcatggag gggtcacgat cggaagcgaa atttccggcg cgtgaagaa cgtcatcgca       960 gagggcaatc ttatggacag cccgaacttg gacagagccc tccgcattaa acgaattcg      1020 gtgcgtggcg gcgttcttga aaacatctac tttcacaaaa atacggtcaa agcttgaag     1080 cgcgaattga tcgccatcga tatggaatat gaagaaggag atgccggaga tttcaaacct    1140
gtcgtccgca cggttggatg tttaacaact gaaaagcatg gcggacatt acgggatcag     1200 ggtgctggca tacgaccact ctccggtcac cgggctgaaa gtggctga                 1248
```

<210> SEQ ID NO 6
<211> LENGTH: 415
<212> TYPE: PRT
<213> ORGANISM: Bacillus licheniformis

<400> SEQUENCE: 6

Leu Arg Tyr Leu Lys Gln Ala Ser His Tyr Lys Gly Ser Gly Asn Val
1               5                   10                  15

Ser Leu Gln Lys Ile Lys Gln Glu Ile Val Lys Lys Leu Lys Val Pro
                20                  25                  30

Val Phe Pro Asn Arg Ser Phe Asp Val Thr Ser Phe Gly Ala Asp Glu
            35                  40                  45

Asn Gly Lys Asn Asp Ser Thr Glu Ala Ile Gln Lys Ala Ile Asp Gln
        50                  55                  60

Ala His Gln Ala Gly Gly Arg Val Thr Val Pro Glu Gly Val Phe
65                  70                  75                  80

Leu Ser Gly Ala Leu Arg Leu Lys Ser Asn Val Asp Leu His Ile Ala
                85                  90                  95

Lys Gly Ala Val Ile Lys Phe Ser Gln Asn Pro Glu Asp Tyr Leu Pro
            100                 105                 110

Val Val Leu Thr Arg Phe Glu Gly Val Glu Leu Tyr Asn Tyr Ser Pro
        115                 120                 125

Leu Ile Tyr Ala Tyr Glu Ala Asp Asn Ile Ala Ile Thr Gly Lys Gly
    130                 135                 140

Thr Leu Asp Gly Gln Gly Asp Asp Glu His Trp Trp Pro Trp Lys Arg
145                 150                 155                 160

Gly Thr Asn Gly Gln Pro Ser Gln Glu Lys Asp Arg Asn Ala Leu Phe
                165                 170                 175

Glu Met Ala Glu Arg Gly Ile Pro Val Thr Glu Arg Gln Phe Gly Lys
            180                 185                 190

Gly His Tyr Leu Arg Pro Asn Phe Ile Gln Pro Tyr Arg Cys Lys His
        195                 200                 205

```
Ile Leu Ile Gln Gly Val Thr Val Leu Asn Ser Pro Met Trp Gln Val
    210                 215                 220
His Pro Val Leu Cys Glu Asn Val Thr Val Asp Gly Ile Lys Val Ile
225                 230                 235                 240
Gly His Gly Pro Asn Thr Asp Gly Val Asn Pro Glu Ser Cys Lys Asn
                245                 250                 255
Val Val Ile Lys Gly Cys His Phe Asp Asn Gly Asp Cys Ile Ala
            260                 265                 270
Val Lys Ser Gly Arg Asn Ala Asp Gly Arg Ile Asn Ile Pro Ser
        275                 280                 285
Glu Asn Ile Val Ile Glu His Asn Glu Met Lys Asp Gly His Gly Gly
    290                 295                 300
Val Thr Ile Gly Ser Glu Ile Ser Gly Val Lys Asn Val Ile Ala
305                 310                 315                 320
Glu Gly Asn Leu Met Asp Ser Pro Asn Leu Asp Arg Ala Leu Arg Ile
                325                 330                 335
Lys Thr Asn Ser Val Arg Gly Gly Val Leu Glu Asn Ile Tyr Phe His
            340                 345                 350
Lys Asn Thr Val Lys Ser Leu Lys Arg Glu Leu Ile Ala Ile Asp Met
        355                 360                 365
Glu Tyr Glu Glu Gly Asp Ala Gly Asp Phe Lys Pro Val Val Arg Thr
    370                 375                 380
Val Gly Cys Leu Thr Thr Glu Lys His Gly Arg Thr Leu Arg Asp Gln
385                 390                 395                 400
Gly Ala Gly Ile Arg Pro Leu Ser Gly His Arg Ala Glu Ser Gly
                405                 410                 415

<210> SEQ ID NO 7
<211> LENGTH: 1026
<212> TYPE: DNA
<213> ORGANISM: Bacillus licheniformis

<400> SEQUENCE: 7
atgaagaaat taatcagcat catctttatc tttgtattag gggttgtcgg gtcattgaca      60
gcggcggttt cggcagaagc agcttctgcc ttaaactcgg gcaaagtaaa tccgcttgcc     120
gacttcagct taaaaggctt tgccgcacta acggcggaa caacgggcgg agaaggcggt      180
cagacggtaa ccgtaacaac gggagatcag ctgattgcgg cattaaaaaa taagaatgca     240
aatacgcctt taaaaattta tgtcaacggc accattacaa catcaaatac atccgcatca     300
aagattgacg tcaaagacgt gtcaaacgta tcgattgtcg gatcagggac caaaggggaa     360
ctcaaaggga tcggcatcaa atatggcgg gccaacaaca tcatcatccg caacttgaaa      420
attcacgagg tcgcctcagg cgataaagac gcgatcggca ttgaaggccc ttctaaaaac     480
atttggggtg atcataatga gctttaccac agcctgaacg ttgacaaaga ttactatgac     540
ggattatttg acgtcaaaag agatgcgaa tatattacat tctcttggaa ctatgtgcac      600
gatggatgga atcaatgct gatgggttca tcggacagcg ataattacaa caggacgatt      660
acattccatc ataactggtt tgagaatctg aattcgcgtg tgccgtcatt ccgtttcgga     720
gaaggccata tttacaacaa ctatttcaat aaaatcatcg acagcggaat taattcgagg     780
atgggcgcgc gcatcagaat tgagaacaac ctctttgaaa acgccaaaga tccgattgtc     840
tcttggtaca gcagttcacc gggctattgg catgtatcca caacaaatt tgtaaactct      900
agggggcagta tgccgactac ctctactaca acctataatc cgccatacag ctactcactc     960
```

-continued

```
gacaatgtcg acaatgtaaa atcaatcgtc aagcaaaatg ccggagtcgg caaaatcaat    1020
ccataa                                                               1026
```

<210> SEQ ID NO 8
<211> LENGTH: 341
<212> TYPE: PRT
<213> ORGANISM: Bacillus licheniformis

<400> SEQUENCE: 8

```
Met Lys Lys Leu Ile Ser Ile Ile Phe Ile Phe Val Leu Gly Val Val
 1               5                   10                  15

Gly Ser Leu Thr Ala Ala Val Ser Ala Glu Ala Ala Ser Ala Leu Asn
            20                  25                  30

Ser Gly Lys Val Asn Pro Leu Ala Asp Phe Ser Leu Lys Gly Phe Ala
        35                  40                  45

Ala Leu Asn Gly Gly Thr Thr Gly Gly Glu Gly Gln Thr Val Thr
 50                  55                  60

Val Thr Thr Gly Asp Gln Leu Ile Ala Ala Leu Lys Asn Lys Asn Ala
 65                  70                  75                  80

Asn Thr Pro Leu Lys Ile Tyr Val Asn Gly Thr Ile Thr Ser Asn
                85                  90                  95

Thr Ser Ala Ser Lys Ile Asp Val Lys Asp Val Ser Asn Val Ser Ile
            100                 105                 110

Val Gly Ser Gly Thr Lys Gly Glu Leu Lys Gly Ile Gly Ile Lys Ile
        115                 120                 125

Trp Arg Ala Asn Asn Ile Ile Ile Arg Asn Leu Lys Ile His Glu Val
130                 135                 140

Ala Ser Gly Asp Lys Asp Ala Ile Gly Ile Glu Gly Pro Ser Lys Asn
145                 150                 155                 160

Ile Trp Val Asp His Asn Glu Leu Tyr His Ser Leu Asn Val Asp Lys
                165                 170                 175

Asp Tyr Tyr Asp Gly Leu Phe Asp Val Lys Arg Asp Ala Glu Tyr Ile
            180                 185                 190

Thr Phe Ser Trp Asn Tyr Val His Asp Gly Trp Lys Ser Met Leu Met
        195                 200                 205

Gly Ser Ser Asp Ser Asp Asn Tyr Asn Arg Thr Ile Thr Phe His His
210                 215                 220

Asn Trp Phe Glu Asn Leu Asn Ser Arg Val Pro Ser Phe Arg Phe Gly
225                 230                 235                 240

Glu Gly His Ile Tyr Asn Asn Tyr Phe Asn Lys Ile Ile Asp Ser Gly
                245                 250                 255

Ile Asn Ser Arg Met Gly Ala Arg Ile Arg Ile Glu Asn Asn Leu Phe
            260                 265                 270

Glu Asn Ala Lys Asp Pro Ile Val Ser Trp Tyr Ser Ser Pro Gly
        275                 280                 285

Tyr Trp His Val Ser Asn Asn Lys Phe Val Asn Ser Arg Gly Ser Met
290                 295                 300

Pro Thr Thr Ser Thr Thr Thr Tyr Asn Pro Pro Tyr Ser Tyr Ser Leu
305                 310                 315                 320

Asp Asn Val Asp Asn Val Lys Ser Ile Val Lys Gln Asn Ala Gly Val
                325                 330                 335

Gly Lys Ile Asn Pro
            340
```

<210> SEQ ID NO 9
<211> LENGTH: 1482
<212> TYPE: DNA
<213> ORGANISM: Bacillus licheniformis

<400> SEQUENCE: 9

```
gcttctgcct taaactcggg caaagtaaat ccgcttgccg acttcagctt aaaaggcttt        60
gccgcactaa acggcggaac aacgggcgga aaggcggtc agacggtaac cgtaacaacg        120
ggagatcagc tgattgcggc attaaaaaat aagaatgcaa atacgccttt aaaaatttat       180
gtcaacggca ccattacaac atcaaataca tccgcatcaa agattgacgt caaagacgtg       240
tcaaacgtat cgattgtcgg atcagggacc aaggggaac tcaaagggat cggcatcaaa        300
atatggcggg ccaacaacat catcatccgc aacttgaaaa ttcacgaggt cgcctcaggc       360
gataaagacg cgatcggcat tgaaggccct tctaaaaaca tttgggttga tcataatgag       420
ctttaccaca gcctgaacgt tgacaaagat tactatgacg gattatttga cgtcaaaaga       480
gatgcggaat atattacatt ctcttggaac tatgtgcacg atggatggaa atcaatgctg       540
atgggttcat cggacagcga taattacaac aggacgatta cattccatca taactggttt       600
gagaatctga attcgcgtgt gccgtcattc cgtttcggag aaggccatat ttacaacaac       660
tatttcaata aaatcatcga cagcggaatt aattcgagga tgggcgcgcg catcagaatt       720
gagaacaacc tctttgaaaa cgccaaagat ccgattgtct cttggtacag cagttcaccg       780
ggctattggc atgtatccaa caacaaattt gtaaactcta ggggcagtat gccgactacc       840
tctactacaa cctataatcc gccatacagc tactcactcg acaatgtcga caatgtaaaa       900
tcaatcgtca agcaaaatgc cggagtcggc aaaatccagc gcagaccgcc aacaccgacc       960
ccgacttcac cgccaagcgc aaatacaccg gtatcaggca atttgaaggt tgaattctac      1020
aacagcaatc cttcagatac tactaactca atcaatcctc agttcaaggt tactaatacc      1080
ggaagcagtg caattgattt gtccaaactc acattgagat attattatac agtagacgga      1140
cagaaagatc agaccttctg tgtgaccat gctgcaataa tcggcagtaa cggcagctac       1200
aacggaatta cttcaaatgt aaaaggaaca tttgtaaaaa tgagttcctc aacaaataac      1260
gcagacacct accttgaaat aagctttaca ggcggaactc ttgaaccggg tgcacatgtt      1320
cagatacaag gtagatttgc aaagaatgac tggagtaact atacacagtc aaatgactac      1380
tcattcaagt ctcgttcaca gtttgttgaa tgggatcagg taacagcata cttgaacggt      1440
gttcttgtat ggggtaaaga acccggtggc agtgtagtat ag                         1482
```

<210> SEQ ID NO 10
<211> LENGTH: 493
<212> TYPE: PRT
<213> ORGANISM: Bacillus licheniformis

<400> SEQUENCE: 10

```
Ala Ser Ala Leu Asn Ser Gly Lys Val Asn Pro Leu Ala Asp Phe Ser
 1               5                  10                  15

Leu Lys Gly Phe Ala Ala Leu Asn Gly Gly Thr Thr Gly Gly Glu Gly
            20                  25                  30

Gly Gln Thr Val Thr Val Thr Thr Gly Asp Gln Leu Ile Ala Ala Leu
        35                  40                  45

Lys Asn Lys Asn Ala Asn Thr Pro Leu Lys Ile Tyr Val Asn Gly Thr
    50                  55                  60

Ile Thr Thr Ser Asn Thr Ser Ala Ser Lys Ile Asp Val Lys Asp Val
```

```
65                  70                  75                  80
Ser Asn Val Ser Ile Val Gly Ser Gly Thr Lys Gly Glu Leu Lys Gly
                85                  90                  95
Ile Gly Ile Lys Ile Trp Arg Ala Asn Asn Ile Ile Arg Asn Leu
            100                 105                 110
Lys Ile His Glu Val Ala Ser Gly Asp Lys Asp Ala Ile Gly Ile Glu
            115                 120                 125
Gly Pro Ser Lys Asn Ile Trp Val Asp His Asn Glu Leu Tyr His Ser
130                 135                 140
Leu Asn Val Asp Lys Asp Tyr Tyr Asp Gly Leu Phe Asp Val Lys Arg
145                 150                 155                 160
Asp Ala Glu Tyr Ile Thr Phe Ser Trp Asn Tyr Val His Asp Gly Trp
                165                 170                 175
Lys Ser Met Leu Met Gly Ser Ser Asp Ser Asp Asn Tyr Asn Arg Thr
            180                 185                 190
Ile Thr Phe His His Asn Trp Phe Glu Asn Leu Asn Ser Arg Val Pro
            195                 200                 205
Ser Phe Arg Phe Gly Glu Gly His Ile Tyr Asn Asn Tyr Phe Asn Lys
            210                 215                 220
Ile Ile Asp Ser Gly Ile Asn Ser Arg Met Gly Ala Arg Ile Arg Ile
225                 230                 235                 240
Glu Asn Asn Leu Phe Glu Asn Ala Lys Asp Pro Ile Val Ser Trp Tyr
                245                 250                 255
Ser Ser Ser Pro Gly Tyr Trp His Val Ser Asn Asn Lys Phe Val Asn
            260                 265                 270
Ser Arg Gly Ser Met Pro Thr Thr Ser Thr Thr Thr Tyr Asn Pro Pro
            275                 280                 285
Tyr Ser Tyr Ser Leu Asp Asn Val Asp Asn Val Lys Ser Ile Val Lys
            290                 295                 300
Gln Asn Ala Gly Val Gly Lys Ile Gln Arg Arg Pro Pro Thr Pro Thr
305                 310                 315                 320
Pro Thr Ser Pro Pro Ser Ala Asn Thr Pro Val Ser Gly Asn Leu Lys
                325                 330                 335
Val Glu Phe Tyr Asn Ser Asn Pro Ser Asp Thr Thr Asn Ser Ile Asn
            340                 345                 350
Pro Gln Phe Lys Val Thr Asn Thr Gly Ser Ser Ala Ile Asp Leu Ser
            355                 360                 365
Lys Leu Thr Leu Arg Tyr Tyr Tyr Thr Val Asp Gly Gln Lys Asp Gln
370                 375                 380
Thr Phe Trp Cys Asp His Ala Ala Ile Ile Gly Ser Asn Gly Ser Tyr
385                 390                 395                 400
Asn Gly Ile Thr Ser Asn Val Lys Gly Thr Phe Val Lys Met Ser Ser
                405                 410                 415
Ser Thr Asn Asn Ala Asp Thr Tyr Leu Glu Ile Ser Phe Thr Gly Gly
            420                 425                 430
Thr Leu Glu Pro Gly Ala His Val Gln Ile Gln Gly Arg Phe Ala Lys
            435                 440                 445
Asn Asp Trp Ser Asn Tyr Thr Gln Ser Asn Asp Tyr Ser Phe Lys Ser
450                 455                 460
Arg Ser Gln Phe Val Glu Trp Asp Gln Val Thr Ala Tyr Leu Asn Gly
465                 470                 475                 480
Val Leu Val Trp Gly Lys Glu Pro Gly Gly Ser Val Val
                485                 490
```

<210> SEQ ID NO 11
<211> LENGTH: 42
<212> TYPE: DNA
<213> ORGANISM: Bacillus licheniformis

<400> SEQUENCE: 11
gtcgccgggg cggccgctat caattggtaa ctgtatctca gc         42

<210> SEQ ID NO 12
<211> LENGTH: 64
<212> TYPE: DNA
<213> ORGANISM: Bacillus licheniformis

<400> SEQUENCE: 12
gtcgcccggg agctctgatc aggtaccaag cttgtcgacc tgcagaatga ggcagcaaga    60
agat                                                                64

<210> SEQ ID NO 13
<211> LENGTH: 61
<212> TYPE: DNA
<213> ORGANISM: Bacillus licheniformis

<400> SEQUENCE: 13
gtcggcggcc gctgatcacg taccaagctt gtcgacctgc agaatgaggc agcaagaaga    60
t                                                                   61

<210> SEQ ID NO 14
<211> LENGTH: 35
<212> TYPE: DNA
<213> ORGANISM: Bacillus licheniformis

<400> SEQUENCE: 14
gtcggagctc tatcaattgg taactgtatc tcagc                35

<210> SEQ ID NO 15
<211> LENGTH: 35
<212> TYPE: DNA
<213> ORGANISM: Bacillus licheniformis

<400> SEQUENCE: 15
aacagctgat cacgactgat cttttagctt ggcac                35

<210> SEQ ID NO 16
<211> LENGTH: 37
<212> TYPE: DNA
<213> ORGANISM: Bacillus licheniformis

<400> SEQUENCE: 16
aactgcagcc gcggcacatc ataatgggac aaatggg              37

<210> SEQ ID NO 17
<211> LENGTH: 39
<212> TYPE: DNA
<213> ORGANISM: Bacillus licheniformis

<400> SEQUENCE: 17
ctaactgcag ccgcggcagc ttctgcctta aactcgggc            39

<210> SEQ ID NO 18
<211> LENGTH: 42
<212> TYPE: DNA

<213> ORGANISM: Bacillus licheniformis

<400> SEQUENCE: 18
gcgttgagac gcgcggccgc tgaatgcccc ggacgtttca cc					42

<210> SEQ ID NO 19
<211> LENGTH: 44
<212> TYPE: DNA
<213> ORGANISM: Bacillus licheniformis

<400> SEQUENCE: 19
cacatctgca gcatgaagag attagcaggt acggttattt tgtc					44

<210> SEQ ID NO 20
<211> LENGTH: 40
<212> TYPE: DNA
<213> ORGANISM: Bacillus licheniformis

<400> SEQUENCE: 20
ctcatcatgc ggccgcaggg gcctttattt gcaatcagtg					40

<210> SEQ ID NO 21
<211> LENGTH: 40
<212> TYPE: DNA
<213> ORGANISM: Bacillus licheniformis

<400> SEQUENCE: 21
cacatctgca gccgcggcag ccgaggtcgt tcacaaaacg					40

<210> SEQ ID NO 22
<211> LENGTH: 40
<212> TYPE: DNA
<213> ORGANISM: Bacillus licheniformis

<400> SEQUENCE: 22
ctcatcatgc ggccgcaggg gcctttattt gcaatcagtg					40

<210> SEQ ID NO 23
<211> LENGTH: 43
<212> TYPE: DNA
<213> ORGANISM: Bacillus licheniformis

<400> SEQUENCE: 23
cataaatctg cagccgcggc agcaaacgaa gattatccgg aac					43

<210> SEQ ID NO 24
<211> LENGTH: 46
<212> TYPE: DNA
<213> ORGANISM: Bacillus licheniformis

<400> SEQUENCE: 24
gaaaggaaaa gcggccgcca aatattgaaa agtgagcgca atgtcg				46

<210> SEQ ID NO 25
<211> LENGTH: 127
<212> TYPE: DNA
<213> ORGANISM: Bacillus licheniformis

<400> SEQUENCE: 25
cgacaatgtc gacaatgtaa atcaatcgt caagcaaaat gccggagtcg gcaaatcca		60 gcgcagaccg ccaacaccga ccccgacttc accgccaagc gcaaatacac cggtatcagg		120 caatttg									127

```
<210> SEQ ID NO 26
<211> LENGTH: 48
<212> TYPE: DNA
<213> ORGANISM: Bacillus licheniformis

<400> SEQUENCE: 26
gcgttgagac gcgcggccgc tataccacac tgccaccggg ttctttac                         48
```

PECTIN DEGRADING ENZYMES FROM BACILLUS LICHENIFORMIS

This application is a continuation of U.S. application Ser. No. 09/198,956, filed Nov. 24, 1998, now U.S. Pat. No. 6,165,769, which a continuation-in-part of U.S. patent application Ser. No. 09/073,684, filed on May 6, 1998 now U.S. Pat. No. 6,124,127. Also, this application claims priority under 35 U. S. C. 119 of Danish application 1344/97 filed Nov. 24, 1997, and benefit of U. S. Provisional application 60/067,240, filed Dec. 2, 1997.

The present invention relates to a pectin degrading enzyme preparation; preferably to microbial pectin degrading enzymes, more specifically to microbial enzymes exhibiting pectin degrading activity as their major enzymatic activity in the neutral and alkaline pH ranges, especially to cloned pectin degrading enzymes derived from *Bacillus licheniformis;* to a method of producing such enzymes; and to methods for using such enzymes in the textile, detergent and cellulose fiber processing industries.

BACKGROUND OF THE INVENTION

Pectin polymers are important constituents of plant cell walls. Pectin is a hetero-polysaccharide with a backbone composed of alternating homogalacturonan (smooth regions) and rhamnogalacturonan (hairy regions). The smooth regions are linear polymers of 1,4-linked alpha-D-galacturonic acid. The galacturonic acid residues can be methyl-esterified on the carboxyl group to a varying degree, usually in a non-random fashion with blocks of polygalacturonic acid being completely methyl-esterified.

Pectinases can be classified according to their preferential substrate, highly methyl-esterified pectin or low methyl-esterified pectin and polygalacturonic acid (pectate), and their reaction mechanism, beta-elimination or hydrolysis. Pectinases can be mainly endo-acting, cutting the polymer at random sites within the chain to give a mixture of oligomers, or they may be exo-acting, attacking from one end of the polymer and producing monomers or dimers. Several pectinase activities acting on the smooth regions of pectin are included in the classification of enzymes provided by the Enzyme Nomenclature (1992) such as pectate lyase (EC 4.2.2.2), pectin lyase (EC 4.2.2.10), polygalacturonase (EC 3.2.1.15), exo-polygalaturonase (EC 3.2.1.67), exo-polygalacturonate lyase (EC 4.2.2.9) and exo-poly-alpha-galacturonosidase (EC 3.2.1.82).

Pectate lyases have been cloned from different bacterial genera such as Erwinia, Pseudomonas, Kiebsiella and Xanthomonas.

Also from *Bacillus subtilis* (Nasser et al. (1993) FEBS 335:319– 326) and *Bacillus* sp. YA-14 (Kim et al. (1994) Biosci. Biotech. Biochem. 58:947–949) cloning of a pectate lyase has been described. Purification of pectate lyases with maximum activity in the pH range of 8–10 produced by *Bacillus pumilus* (Dave and Vaughn (1971) J. Bacteriol. 108:166–174), *B. polymyxa* (Nagel and Vaughn (1961) Arch. Biochem. Biophys. 93:344–352), *B. stearothermophilus* (Karbassi and Vaughn (1980) Can. J. Microbiol. 26:377–384), Bacillus sp. (Hasegawa and Nagel (1966) J. Food Sci. 31:838–845) and Bacillus sp. RK9 (Kelly and Fogarty (1978) Can. J. Microbiol. 24:1164–1172) has been reported, however, no publication was found on cloning of pectate lyase encoding genes from these organisms. All the pectate lyases described require divalent cations for maximum activity, calcium ions being the most stimulatory.

WO 98/45393 discloses detergent compositions containing protopectinase with remarkable detergency agains muddy soilings.

Generally, pectinase producing microorganisms exhibit a broad range of pectin degrading or modifying enzymes. Often the microorganisms also produce cellulases and/or hemicellulases and complex multi-component enzyme preparations from such microorganisms may be difficult to optimise for various applications, they even may contain enzymes with detrimental effect. Thus, it is an object of the present invention to provide a pectin degrading enzyme exhibiting only the desired effects e.g. in detergents or different industrial processes.

SUMMARY OF THE INVENTION

The inventors have now found several pectin degrading enzymes, especially alkaline pectin degrading enzymes, which are endogeneous to a bacterial strain of the genus Bacillus, more specifically to the strain *Bacillus licheniformis,* and have succeeded in identifying DNA sequences encoding such enzymes.

Accordingly, in a first aspect the present invention relates to an enzyme preparation consisting essentially of a pectin degrading enzyme derived from or endogeneous to a strain of *Bacillus licheniformis* or highly related Bacillus species, the enzyme preferably being a pectate lyase (EC 4.2.2.2), a pectin lyase (EC 4.2.2.10) or a polygalacturonase (EC 3.2.1.15).

The DNA sequences of two pectate lyases of the invention are listed in the sequence listing as SEQ ID No. 3 and 7, respectively, and the deduced amino acid sequences are listed in the sequence listing as SEQ ID No. 4 and 8, respectively. It is believed that these novel enzyme will be classified according to the Enzyme Nomenclature in the Enzyme Class EC 4.2.2.2. However, it should be noted that the enzyme of the invention also exhibits catalytic activity on pectin (which may be esterified) besides the activity. on pectate and polygalacturonides conventionally attributed to enzymes belonging to EC 4.2.2.2.

The DNA sequence of a pectin lyase of the invention is listed in the sequence listing as SEQ ID No. 1 and the deduced amino acid sequence is listed in the sequence listing as SEQ ID No. 2. It is believed that this novel enzyme will be classified according to the Enzyme Nomenclature in the Enzyme Class EC 4.2.2.10.

The DNA sequence of a polygalacturonase of the invention is listed in the sequence listing as SEQ ID No. 5 and the deduced amino acid sequence is listed in the sequence listing as SEQ ID No. 6. It is believed that this novel enzyme will be classified according to the Enzyme Nomenclature in the Enzyme Class EC 3.2.1.15.

Accordingly, in a second aspect, the present invention relates to a pectate lyase which is i) a polypeptide produced by *Bacillus licheniformis,* ATCC 14580, or ii) a polypeptide comprising an amino acid sequence as shown in positions 28–341. of SEQ ID NO:8, or iii) an analogue of the polypeptide defined in i) or ii) which is at least 45% homologous with said polypeptide, or iv) is derived from said polypeptide by substitution, deletion or addition of one or several amino acids, provided that the arginines in position 233 and 238 are conserved and the derived polypeptide is at least 42% homologous with said polypeptide, or v) is immunologically reactive with a polyclonal antibody raised against said polypeptide in purified form.

Within one aspect, the present invention provides an isolated polynucleotide molecule selected from the group consisting of (a) polynucleotide molecules encoding a polypeptide having pectate lyase activity and comprising a sequence of nucleotides as shown in SEQ ID No: 10: 7 from nucleotide 82 to nucleotide 1026; (b) species homologs of (a); (c) polynucleotide molecules that encode a polypeptide having pectate lyase activity that is at least 70% identical to the amino acid sequence of SEQ ID NO: 8 from amino acid residue 28 to amino acid residue 341; (d) molecules complementary to (a), (b) or (c); and (e) degenerate nucleotide sequences of (a), (b), (c) or (d).

The plasmid pSJ1678 comprising the polynucleotide molecule (the DNA sequence) encoding the pectate lyase of the present invention as represented by the amino acid sequence SEQ ID NO:8 has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Sep. 25, 1997 under the deposition number DSM 11789.

In a third aspect, the present invention relates to a pectate lyase which is i) a polypeptide produced by *Bacillus licheniformis*, ATCC 14580, or ii) a polypeptide comprising an amino acid sequence as shown in positions 28–221 of SEQ ID NO:4, or iii) an analogue of the polypeptide defined in i) or ii) which is at least 60% homologous with said polypeptide, or iv) is derived from said polypeptide by substitution, deletion or addition of one or several amino acids, provided that the lysines in positions 133 and 155 and the arginine in position 158 are conserved and the derived polypeptide is at least 66% homologous with positions 60–158 of SEQ ID NO:4, or v) is immunologically reactive with a polyclonal antibody raised against said polypeptide in purified form.

Within one aspect, the present invention provides an isolated polynucleotide molecule selected from the group consisting of (a) polynucleotide molecules encoding a polypeptide having pectate lyase activity and comprising a sequence of nucleotides as shown in SEQ ID NO: 3 from nucleotide 82 to nucleotide 666; (b) species homologs of (a); (c). polynucleotide molecules that encode a polypeptide having pectate lyase activity that is at least 70% identical to the amino acid sequence of SEQ ID NO: 4 from amino acid residue 28 to amino acid residue 221; (d) molecules complementary to (a), (b) or (c); and (e) degenerate nucleotide sequences of (a), (b), (c) or (d).

In a fourth aspect, the present invention relates to a pectin lyase which is i) a polypeptide produced by *Bacillus licheniformis*, ATCC 14580, or ii) a polypeptide comprising an amino acid sequence as shown in positions 31–494 of SEQ ID NO:2, or iii) an analogue of the polypeptide defined in i) or ii) which is at least 60% homologous with said polypeptide, or iv) is derived from said polypeptide by substitution, deletion or addition of one or several amino acids, provided that the arginins in positions 377 and 383 relative to SEQ ID NO:2 are conserved and that the derived polypeptide is at least 60% homologous with said polypeptide, or v) is immunologically reactive with a polyclonal antibody raised against said polypeptide in purified form.

Within one aspect, the present invention provides an isolated polynucleotide molecule selected from the group consisting of (a) polynucleotide molecules encoding a polypeptide having pectin lyase activity and comprising a sequence of nucleotides as shown in SEQ ID NO: 1 from nucleotide 91 to nucleotide 1485; (b) species homologs of (a); (c) polynucleotide molecules that encode a polypeptide having pectin lyase activity that is at least 70% identical to the amino acid sequence of SEQ ID NO: 2 from amino acid residue 31 to amino acid residue 494; (d) molecules complementary to (a), (b) or (c); and (e) degenerate nucleotide sequences of (a), (b), (c) or (d).

The plasmid pSJ1678 comprising the polynucleotide molecule (the DNA sequence) encoding the pectin lyase of the present invention as represented by the amino acid sequence SEQ ID NO:2 has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Feb. 23, 1998 under the deposition number DSLM 12031.

In a fifth aspect, the present invention relates to a polygalacturonase which is i) a polypeptide produced by *Bacillus licheniformis*, ATCC 14580, or ii) a polypeptide comprising an amino acid sequence as shown in positions 1–415 of SEQ ID NO:6, or iii) an analogue of the polypeptide defined in i) or ii) which is at least 70% homologous with said polypeptide, is derived from said polypeptide by substitution, deletion or addition of one or several amino acids, or is immunologically reactive with a polyclonal antibody raised against said polypeptide in purified form.

Within one aspect, the present invention provides an isolated polynucleotide molecule selected from the group consisting of (a) polynucleotide molecules encoding a polypeptide having polygalacturonase activity and comprising a sequence of nucleotides as shown in SEQ ID NO: 5 from nucleotide 1 to nucleotide 1248; (b) species homologs of (a); (c) polynucleotide molecules that encode a polypeptide having polygalacturonase activity that is at least 70% identical to the amino acid sequence of SEQ ID NO: 6 from amino acid residue 1 to amino acid residue 415; (d) molecules complementary to (a), (b) or (c); and (e) degenerate nucleotide sequences of (a), (b), (c) or (d).

The plasmid pSJ1678 comprising the polynucleotide molecule (the DNA sequence) encoding the polygalacturonase of the present invention as represented by the amino acid sequence SEQ ID NO:2 has been transformed into a strain of the *Escherichia coil* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Feb. 23, 1998 under the deposition number DSM 12030.

Within other aspects of the invention there is provided an expression vector comprising the following operably linked elements: a transcription promoter; a DNA segment selected from the group consisting of (a) polynucleotide molecules encoding a polypeptide having pectate lyase activity and comprising a sequence of nucleotides as shown in SEQ ID NO: 7 from nucleotide 82 to nucleotide 1026, or as shown in SEQ ID NO; 3 from nucleotide 92 to nucleotide 666; or encoding a polypeptide having pectin lyase activity and comprising a sequence of nucleotides as shown in SEQ ID NO: 1 from nucleotide 91 to nucleotide 1485; or encoding a polypeptide having polygalacturonase activity and comprising a sequence of nucleotides as shown. in SEQ ID NO: 5 from nucleotide 1 to nucleotide 1248; (b) species homologs of (a); (c) polynucleotide molecules that encode a polypeptide having pectate lyase activity that is at least 70% identical to the amino acid sequence of SEQ ID NO: 8 from amino acid residue 28 to amino acid residue 341 or to the amino acid sequence of SEQ ID NO: 4 from amino acid residue 28 to amino acid residue 221; or encode a polypeptide having pectin lyase activity that is at least 70%. identical to the amino acid sequence of SEQ ID NO: 2 from amino acid residue 31 to amino acid residue and 494; encode a polypeptide having polygalacturonase activity that is at least 70% identical to the amino acid sequence of SEQ ID NO: 6 from amino acid residue 1 to amino acid residue 415; (d) degenerate nucleotide sequences of (a), (b), or (c); and a transcription terminator.

Within yet another aspect of the present invention there is provided a cultured cell into which has been introduced an expression vector as disclosed above, wherein said cell expresses the polypeptide encoded by the DNA segment.

A further aspect of the present invention provides an isolated polypeptide having pectate lyase activity selected from the group consisting of (a) polypeptide molecules comprising a sequence of amino acid residues as shown in SEQ ID NO:8 from amino acid residue 28 to amino acid residue 341; (b) polypeptide molecules comprising a sequence of amino acid residues as shown in SEQ ID NO:4 from amino acid residue 28.to amino acid residue 221; and (c) species homologs of (a) or (b).

Another aspect of the present invention provides an isolated polypeptide having pectin lyase activity selected from the group consisting of (a) polypeptide molecules comprising a sequence of amino acid residues as shown in SEQ ID NO:2 from amino acid residue 31 to amino acid residue 494; and (b) species homologs of (a).

Another aspect of the present invention provides an isolated polypeptide having polygalacturonase activity selected from the group consisting of (a) polypeptide molecules comprising a sequence of amino acid residues as shown in SEQ ID NO:6 from amino acid residue 1 to amino acid residue 415; and (b) species homologs of (a).

Within another aspect of the present invention there is provided a composition comprising a purified polypeptide according to the invention in combination with other polypeptides.

Within another aspect of the present invention there are provided methods for producing a polypeptide according to the invention comprising culturing a cell into which has been introduced an expression vector as disclosed above, whereby said cell expresses a polypeptide encoded by the DNA segment and recovering the polypeptide.

The novel enzyme of the present invention is useful for the treatment of cellulosic material, especially cellulose-containing fiber, yarn, woven or non-woven fabric, treatment of mechanical paper-making pulps or recycled waste paper, and for retting of fibres. The treatment can be carried out during the processing of cellulosic material into a material ready for garment manufacture or fabric manufacture, e.g. in the desizing or scouring step; or during industrial or household laundering of such fabric or garment.

Accordingly, in further aspects the present invention relates to a detergent composition comprising an enzyme having substantial pectin degrading activity; and to use of the enzyme of the invention for the treatment of cellulose-containing fibers, yarn, woven or non-woven fabric.

The enzymes of the invention are very effective for use in an enzymatic scouring process in the preparation of cellulosic material e.g. for proper response in subsequent dyeing operations. Further, it is contemplated that detergent compositions comprising the novel enzymes are capable of removing or bleaching certain soils or stains present on laundry, especially soils and spots resulting from galactan or arabinogalactan containing food, plants, and the like. It is also contemplated that treatment with detergent compositions comprising the novel enzyme can prevent binding of certain soils to the cellulosic material. The enzymes of the invention are also useful as ingredients in hard surface cleaning compositions having the effect of removing or assisting in removing certain soils or stains from hard surfaces in need of cleaning.

Definitions

Prior to discussing this invention in further detail, the following terms will first be defined.

The term "ortholog" (or "species homolog") denotes a polypeptide or protein obtained from one species that has homology to an analogous polypeptide or protein from a different species.

The term "paralog" denotes a polypeptide or protein obtained from a given species that has homology to a distinct polypeptide or protein from that same species.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector it is to be introduced. Thus, the vector may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinantly expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention) which originate from the homologous cell where the polypeptide of the invention is originally obtained from.

The term "obtained from" as used herein in connection with a specific microbial source, means that the polynucleotide and/or polypeptide is produced by the specific source, or by a cell in which a gene from the source have been inserted.

The term "endogeneous to" as used herein in connection With a specific microbial source, means that a polypeptide is produced by the specific source due to the presence in the source of a native gene, ie a gene which has not been recombinantly inserted into a cell of the source.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "pectin" denotes pectate, polygalacturonic acid, and pectin which may be esterified to a higher or lower degree.

The term "pectin degrading enzyme" or "pectinase" denotes a pectinase enzyme defined according to the art where pectinases are a group of enzymes that cleave glycosidic linkages of pectic substances mainly poly(1,4-alpha-D-galacturonide and its derivatives (Sakai et al., 1993).

Preferably a pectinase of the invention is a pectinase which is a pectinase enzyme which catalyzes the random cleavage of alpha-1,4-glycosidic linkages in pectic acid also called polygalacturonic acid by transelimination such as the enzyme class polygalacturonate lyase (EC 4.2.2.2) (PGL) also known as poly(1,4-alpha-D-galacturonide) lyase also known as pectate lyase. Also preferred is a pectinase enzyme which catalyzes the random hydrolysis of alpha-1,4-glycosidic linkages in pectic acid such as the enzyme class polygalacturonase (EC 3.2.1.15) (PG) also known as endo-PG. Also preferred is a pectinase enzyme such as polymethylgalcturonate lyase (EC 4.2.2.10) (PMGL), also known as Endo-PMGL, also known as poly (methyoxygalacturonide)lyase also known as pectin lyase which catalyzes the random cleavage of alpha-1,4-glycosidic linkages of pectin.

DETAILED DESCRIPTION OF THE INVENTION

How To Use A Sequence Of The Invention To Get Other Related Sequences

The disclosed sequence information herein relating to a polynucleotide sequence encoding a pectate lyase of the invention can be used as a tool to identify other homologous pectate lyases. For instance, polymerase chain reaction (PCR) can be used to amplify sequences encoding other homologous pectate lyases from a variety of microbial sources, in particular of different Bacillus species.

Polynucleotides

Within preferred embodiments of the invention an isolated polynucleotide of the invention will hybridize to similar sized regions of SEQ ID No. 1, 3, 5 or 7, respectively, or a sequence complementary thereto, under at least medium stringency conditions.

In particular polynucleotides of the invention will hybridize to a denatured double-stranded DNA probe comprising either the full sequence (encoding the mature part of the polypeptide) shown in positions 91–1485 of SEQ ID NO:1, in positions 82–666 of SEQ ID NO:3, in positions 1–1248 of SEQ ID NO:5 or in positions 82–1026of SEQ ID NO:7, or any probe comprising a subsequence of SEQ ID NO:1, 3, 5 or 7, respectively, having a length of at least about 100 base pairs under at least medium stringency conditions, but preferably at high stringency conditions as described in detail below. Suitable experimental conditions for determining hybridization at medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity higher than 1×109 cpm/µg) probe for 12 hours at ca. 45° C. The filter is then washed twice for 30 minutes in 2×SSC, 0.5 % SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

As previously noted, the isolated polynucleotides of the present invention include DNA and RNA. Methods for isolating DNA and RNA are well known in the art. DNA and RNA encoding genes of interes can be cloned in Gene Banks or DNA libraries by means of methods known in the art.

Polynucleotides encoding polypeptides having pectate lyase activity of the invention are then identified and isolated by, for example,, hybridization or PCR.

The present invention further provides counterpart polypeptides and polynucleotides from different bacterial strains (orthologs or paralogs). Of particular interest are pectin degrading polypeptides from gram-positive alkalophilic strains, including species of Bacillus.

Species homologues of polypeptides exhibiting pectin degrading activity of the invention can be cloned using information and compositions provided by the present invention in combination with conventional cloning techniques. For example, DNA can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA encoding an polypeptide having pectin degrading activity of the invention can then be isolated by a variety of methods, such as by probing with a complete or partial DNA or with one or more sets of degenerate probes based on the disclosed sequences. A DNA can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (monoclonal or polyclonal) raised against the pectate lyases, pectin lyase or polygalacturonase cloned from *B. licheniformis*, ATCC 14580, expressed and purified as described in Materials and Methods and the Examples, or by an activity test relating to a polypeptide having pectin degrading activity. Similar techniques can also be applied to the isolation of genomic clones.

The polypeptide encoding part of the DNA sequence cloned into plasmid pSJ1678 present in *Escherichia coli* DSM 11789 and in *Escherichia coli* DSM 12030 and in *Escherichia coli* DSM 12031 and/or an analogue DNA sequence, of the invention may be cloned from a strain of the bacterial species *Bacillus licheniformis*, preferably the strain ATCC 14580, producing the enzyme with pectin degrading activity, or another or related organism as described herein.

Alternatively, the analogous sequence may be constructed on the basis of the DNA sequence obtainable from the plasmid present in *Escherichia coli* DSM 11789, in *Escherichia coli* DSM 12030 or in *Escherichia coli* DSM 12031, e.g be a sub-sequence thereof, and/or by introduction of nucleotide substitutions which do not give rise to another amino acid sequence of the pectin degrading enzyme encoded by the DNA sequence, but which corresponds to the codon usage of the host organism intended for production of the enzyme, or by introduction of nucleotide substitutions which may give rise to a different amino acid sequence (i.e. a variant of the pectin degrading enzyme of the invention).

Based on the sequence information disclosed herein a full length DNA sequence encoding a pectinase of the invention and comprising the DNA sequence shown in SEQ ID No 1, 3, 5 or 7, respectively, may be cloned.

Cloning is performed by standard procedures known in the art such as by, preparing a genomic library from a Bacillus strain;
plating such a library on suitable substrate plates;
identifying a clone comprising a polynucleotide sequence of the invention by standard hybridization techniques using a probe based on SEQ ID No 1, 3, 5 or 7, respectively; or by identifying a clone from said *Bacillus licheniformis* ATCC 14580 genomic library by an Inverse PCR strategy using primers based on sequence information from SEQ ID No 1, 3, 5 or 7, respectively. Reference is made to M. J. MCPherson et al. ("PCR A practical approach" Information Press Ltd, Oxford England) for further details relating to Inverse PCR.

Based on the sequence information disclosed herein (SEQ ID Nos 1, 2, 3, 4, 5, 6, 7 and 8) is it routine work for a person skilled in the art to isolate homologous polynucleotide sequences encoding homologous pectinases of the invention by a similar strategy using genomic libraries from related microbial organisms, in particular from genomic libraries from other strains of the genus Bacillus such as *Bacillus subtilis*.

Alternatively, the DNA encoding the pectin degrading enzyme of the invention may, in accordance with well-known procedures, conveniently be cloned from a suitable source, such as any of the below mentioned organisms, by use of synthetic oligonucleotide probes prepared on the basis of the DNA sequence obtainable from the plasmid present in *Escherichia coli* DSM 11789, in *Escherichia coli* DSM 12030 or in *Escherichia coli* DSM 12031.

Accordingly, the polynucleotide molecule of the invention may be isolated from *Escherichia coli*, DSM 11789, *Escherichia coli* DSM 12030 , or *Escherichia coli,* DSM 12031, in which the plasmid obtained by cloning such as described above is deposited. Also, the present invention relates to an isolated substantially pure biological culture of the strain *Escherichia coli,* DSM 11789, *Escherichia coli,* DSM 12030, and *Escherichia coli,* DSM 12031, respectively.

Polypeptides

The sequence of amino acids no. 28–221 of SEQ ID No 4 is a mature pectate lyase sequence; positions 1–27 are the prosequence. The sequence of amino acids no. 28–341 of SEQ ID No 8 is a mature pectate lyase sequence; positions 1–27 are the prosequence. The sequence of amino acids no. 31–494 of SEQ ID No 2 is a mature pectin lyase sequence, positions 1–30 are the prosequence. The sequence of amino acids no. 1–415 of SEQ ID No 6 is a mature polygalacturonase sequence.

The present invention also provides pectin degrading polypeptides that are substantially homologous to the polypeptides of SEQ ID NO:2, 4, 6 and 8, respectively, and their species homologs (paralogs or orthologs. The term "substantially homologous" is used herein to denote polypeptides having at least 60%, preferably at least 70%, more preferably at least 85%, and even more preferably at least 90%, sequence identity to the sequence shown in SEQ ID NO:2, 4, 6 and 8, respectively, or their orthologs or paralogs. Such polypeptides will more preferably be at least 95% identical, and most preferably 98% or more identical to the sequence shown in SEQ ID NO:2, 4, 6 and 8, respectively, or its orthologs or paralogs. Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

The present invention is based in part upon the discovery of several novel polynucleotide sequences obtained from a *Bacillus licheniformis* strain which encode polypeptide sequences which have homology to other microbial amino acid pectinase sequences.

The new *Bacillus licheniformis* pectinases have been designated:

I: pectate lyase (EC 4.2.2.2)

II: pectate lyase (EC 4.2.2.2)

III: pectin lyase (EC 4.2.2.10)

IV: polygalacturonase (EC 3.2.1.15)

The novel pectinase polypeptide sequences of the present invention were initially identified by querying representative search sequences, specifically amino acid sequences of known pectinases, to the *Bacillus licheniformis* sequence database to identify homologous sequences to pectinases.

Using a conventional percent sequence identity program as described in further details herein (vide infra) the amino acid sequence identity of the amino acid sequences of the appended SEQ ID NOS: 2 (III), 4 (I), 6 (IV), 8 (II) to the closesst prior art known pectinases are shown in tables 1, 2 and 3 below.

TABLE 1

Homology between amino acid sequences for pectate lyases (I)

Most homologous pectin degrading protein to the pectate lyase (I) of this invention is the *B. sp.* strain KSM-P15 found in the International Patent Application published as WO 98/45393 as SEQ ID NO:1 which is 58.8% homologous to the mature protein sequence SEQ ID NO: 4.

TABLE 2

Homology between amino acid sequences for pectate lyases (II)

The sequence used for similarity are the protein sequences from TREMBLREL with the locus listed in the scheme.
II: Amino acid sequence ot the invention (SEQ ID NO:8)
B: o08454.sp_bacteria Amycolata sp. *Pectate lyase*
C: q00893.sp_fungi *Glomereila cingulata*

|    | II    | B     | C     |
|----|-------|-------|-------|
| II | 100%  | 40.8% | 40.5% |
| B  | 40.8  | 100%  |       |
| C  | 40.5% |       | 100%  |

TABLE 3

Homology between amino acid sequences for pectin lyases (III)

Most homologous pectin degrading proteins to the pectin lyase of this invention are the *B. subtilis* pectin lyase O34819 and the *B. subtilis* pectin lyase P94449, both protein sequences found in the TREMBL data base (EMBL/GENBANK/DDBJ DATA BANKS). They are 55% homologous to the protein sequence SEQ ID NO: 2.

TABLE 4

Homology between amino acid sequences for polygalacturonases

The sequences used for simularity are the protein sequences from SWISSPRCT with the locus listed in the scheme.
IV: Amino acid sequence of tne invention (SEQ ID NO:6)
B: p27644.swissprot_bacteria *Agrobacterium tumefaciens*
C: p20041.swissprot_bacteria *Burkholdaria solanacearum*

|    | IV    | B     | C     |
|----|-------|-------|-------|
| IV | 100%  | 36.6% | 30.2% |
| B  | 36.6% |       | 100%  |
| C  | 30.2% |       | 100%  |

The enzyme preparation of the invention is preferably derived from a microorganism, preferably from a bacterium, an archea or a fungus, especially from a bacterium such as a bacterium belonging to Bacillus, preferably to an alkalophilic Bacillus strain which may be selected from the group consisting of the species *Bacillus licheniformis* and highly related Bacillus species in which all species preferably are at least 99% homologous to *Bacillus licheniformis* based on aligned 16S rDNA sequences.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

TABLE 5

Conservative amino acid substitutions

| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the pectate lyase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e pectin degrading activity) to identify amino acid residues that are critical to the activity of the molecule. See also, Hilton et al., *J. Biol. Chem.* 271:4699–4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example,de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86:2152–2156, 1989), WO95/17413, or WO 95/22625. Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223, 409; Huse, WIPO Publication WO 92/06204) and region-directed mutagenesis (Derbyshire et al., *Gene* 46:145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 31 to 494 of SEQ ID NO: 2 (the mature protein), residues 28 to 221 of SEQ ID NO: 4, residues 1 to 415 of SEQ ID NO: 6, and residues 28 to 341 of SEQ ID NO: 8 and retain the pectin degrading activity of the wild-type protein.

The present invention relates in one aspect to a pectin lyase enzyme having the amino acid sequence of positions 31–494 SEQ ID No:2 or an amino sequence derived therefrom by deletion, replacement or addition of one or more amino acid residues (hereinafter referred to as mutation) provided that the pectin lyase is not deactivated and the mutation conserves arginine at the 377th position and arginine at the 383rd position of SEQ ID No:2. Also, the degree of mutation is not particularly limited provided that the above described arginine in the 377th position and the 383rd position are conserved. Preferably, 56% or higher homology exists between such mutation variants of the native or parent pectin lyase enzyme, calculated on the partial sequence corresponding to amino acid positions 31 to 375 of SEQ ID No:2. More preferably, the homology is 70% or higher, particularly 80% or higher.

Further, the present invention relates in one aspect to a pectate lyase enzyme having the amino acid sequence of positions 28–221 SEQ ID No:4 or an amino sequence derived therefrom by deletion, replacement or addition of one or more amino acid residues (hereinafter referred to as mutation) provided that the pectin lyase is not deactivated and the mutation conserves the lysines in positions 133 and 155 and the arginine in position 158 of SEQ ID No:4. Also, the degree of mutation is not particularly limited provided that the above described K133, dK55 and R158 are conserved. Preferably, 66% or higher homology exists between such mutation variants of the native or parent pectin lyase enzyme, calculated on the partial sequence corresponding to amino acid positions 60 to 158 of SEQ ID No:4.

More preferably, the homology is 70% or higher, particularly 80% or higher.

Further, the present invention relates in one aspect to a pectate lyase enzyme having the amino acid sequence of positions 28–341 of SEQ ID No:8 or an amino sequence derived therefrom by deletion, replacement or addition of one or more amino acid residues (hereinafter referred to as mutation) provided that the pectin lyase is not deactivated and the mutation conserves the arginines in position 233 and 238 (R233 and R238) of SEQ ID NO:8. Also, the degree of mutation is not particularly limited provided that the above described R233 and R238 are conserved. Preferably, 42% or higher homology exists between such mutation variants of the native or parent pectin lyase enzyme, calculated on the mature sequence of SEQ ID No:8. More preferably, the homology is 50% or higher, even more preferably higher than 60%, particularly 70% or higher, especially 80% or higher.

The pectin degrading enzyme of the invention may, in addition to the enzyme core comprising the catalytically domain, also comprise a cellulose binding domain (CBD), the cellulose binding domain and enzyme core (the catalytically active domain) of the enzyme being operably linked. The cellulose binding domain (CBD) may exist as an integral part of the encoded enzyme, or a CBD from another origin may be introduced into the pectin degrading enzyme thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I–X), and demonstrates that CBDs are found in various enzymes such as cellulases, xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the pectin degrading enzyme and growing the host cell to express the fused gene. Enzyme hybrids may be described by the following formula:

CBD-MR-X wherein CBD is the N-terminal or the C-terminal region of an amino acid sequence corresponding to at least the cellulose-binding domain; MR is the middle region. (the linker), and may be a bond, or a short linking group preferably of from about 2 to about 100 carbon atoms, more preferably of from 2 to 40 carbon atoms; or is preferably from about 2 to to about 100 amino acids, more preferably of from 2 to 40 amino acids; and X is an N-terminal or C-terminal region of the pectin degrading enzyme of the invention.

Preferably, the enzyme of the present invention has its maximum catalytic activity at a pH of at least 8, more preferably of at least 8.5, more preferably of at least 9, more preferably of at least 9.5, more preferably of at least 10, even more preferably of at least 10.5, especially of at least 11; and preferably the maximum activity of the enzyme is obtained at a temperature of at least 50° C., more preferably of at least 55° C.

Protein Production

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Bacterial cells, particularly cultured cells of gram-positive organisms, are preferred. Gram-positive cells from the genus of Bacillus are especially preferred, such as *Bacillus subtilis, Bacillus lentus, Bacillus brevis, Bacillus stearothermophilus, Bacillus alkalophilus, Bacillus amyloliquefaciens, Bacillus coagulans, Bacillus circulans, Bacillus clausii, Bacillus lautus, Bacillus thuringiensis, Bacillus agaradhaerens,* or in particular *Bacillus licheniformis.* ATCC 14580 is the type strain of *Bacillus licheniformis.*

Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989; Ausubel et al. (eds.), *Current Protocols in Molecular Biology,* John Wiley and Sons, Inc., NY, 1987; and *Bacillus subtilis* and Other Gram-Positive Bacteria, Sonensheim et al., 1993, American Society for Microbiology, Washington D.C., which are incorporated herein by reference.

In general, a DNA sequence encoding a pectate lyase of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the polypeptide, or may be derived from another secreted protein or synthesized de novo. Numerous suitable secretory signal sequences are known in the art and reference is made to (*Bacillus subtilis* and Other Gram-Positive Bacteria, Sonensheim et al., 1993, American Society for Microbiology, Washington D.C.; and Cutting, S. M.(eds.) "Molecular Biological Methods for Bacillus". John Wiley and Sons, 1990) for further description of suitable secretory signal sequences especially for secretion in a Bacillus host cell. The secretory signal sequence is joined to the DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

The polypeptides of the present invention may also be produced by fermenting a wildtype strain belonging to the genus Bacillus, preferably a strain which may be selected from the group consisting of the species *Bacillus licheniformis* and highly related Bacillus species in which all species are at least 99% homologous to *Bacillus licheniformis* based on aligned 16S rDNA sequences. A specific and highly preferred example is to *Bacillus licheniformis,* ATCC 14580.

Further, the polypeptides of the present invention may be produced by fermenting a mutant or a variant derived from the above mentioned strain. Such a mutant may be obtained by using conventional techniques and selection for mutants giving higher pectinase activity.

The fermentation may be carried out by cultivation of the strain under aerobic conditions in a nutrient medium containing carbon and nitrogen sources together with other essential nutrients, the medium being composed in accordance with the principles of the known art. The medium may be a complex rich medium or a minimal medium. The nitrogen source may be of inorganic and/or organic nature. Suitable inorganic nitrogen sources are nitrates and ammonium salts. Among the organic nitrogen sources quite a number are used regularly in fermentations. Examples are soybean meal, casein, corn, corn steep liquor, yeast extract, urea and albumin. Suitable carbon sources are carbohydrates or carbohydrate containing materials. Preferable the nutrient medium contains pectate, polygalacturonic acid and/or pectin esterified to a higher or lower degree as carbon source and/or inducer of pectinase production. Alternatively, the medium contains a pectin rich material such as soybean meal, apple pulp or citrus peel.

Since the Bacillus species of this invention are alkalophilic the cultivation is preferably conducted at alkaline pH values such as at least pH 8. or at least pH 9, which can be obtained by addition of suitable buffers such as sodium carbonate or mixtures of sodium carbonate and sodium bicarbonate after sterilisation of the growth medium.

It is contemplated that fermentation of a wildtype strain or mutant in a suitable medium can result in a yield of at least 0.5 g of pectinase protein per liter of culture broth or even at least 1 g/l or 2 g/l.

Protein Isolation

When the expressed wild-type or recombinant polypeptide is secreted the polypeptide may be purified from the growth media. Preferably the expression host cells are removed from the media before purification of the polypeptide (e.g. by centrifugation).

When the expressed recombinant polypeptide is not secreted from the host cell, the host cell are preferably disrupted and the polypeptide released into an aqueous "extract" which is the first stage of such purification techniques. Preferably the expression host cells are removed from the media before the cell disruption (e.g. by centrifugation).

The cell disruption may be performed by conventional techniques such as by lysozyme digestion or by forcing the cells through high pressure. See (Robert K. Scobes, Protein Purification, Second edition, Springer-Verlag) for further description of such cell disruption techniques.

Whether or not the expressed recombinant polypeptides (or chimeric polypeptides) is secreted or not it can be purified using fractionation and/or conventional purification methods and media.

Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers.

Selection of a particular method is a matter of routine design and is determined in part by the properties of the chosen support. See, for example, *Affinity Chromatography: Principles & Methods,* Pharmacia LKB Biotechnology, Uppsala, Sweden, 1988.

Polypeptides of the invention or fragments thereof may also be prepared through chemical synthesis. Polypeptides of the invention may be monomers or multimers; glycosylated or non-glycosylated; pegylated or non-pegylated; and may or may not include an initial methionine amino acid residue.

Accordingly, in a further aspect, the present invention also relates to a method of producing the enzyme preparation of the invention, the method comprising culturing a microorganism capable of producing the pectate lyase under conditions permitting the production of the enzyme, and recovering the enzyme from the culture. Culturing may be carried out using conventional fermentation techniques, e.g. culturing in shake flasks or fermentors with agitation to ensure sufficient aeration on a growth medium inducing production of the pectate lyase enzyme. The growth medium may contain a conventional N-source such as peptone, yeast extract or casamino acids, a reduced amount of a conventional C-source such as dextrose or sucrose, and an inducer such as pectate or pectin or composit plant substrates such as cereal brans (e.g. wheat bran or rice husk). The recovery may be carried out using conventional techniques, e.g. separation of bio-mass and supernatant by centrifugation or filtration, recovery of the supernatant or disruption of cells if the enzyme of interest is intracellular, perhaps followed by further purification as described in EP 0 406 314 or by crystallization as described in WO 97/15660.

In yet another aspect, the present invention relates to an isolated pectin degrading enzyme having the properties described above and which is free from homologous impurities, and is produced using conventional recombinant techniques.

Transgenic Plants

The present invention also relates to a transgenic plant, plant part or plant cell which has been transformed with a DNA sequence encoding the pectin degrading enzyme of the invention so as to express and produce this enzyme in recoverable quantities. The enzyme may be recovered from the plant or plant part. Alternatively, the plant or plant part containing the recombinant enzyme may be used as such.

The transgenic plant can be dicotyledonous or monocotyledonous, for short a dicot or a monocot. Examples of monocot plants are grasses, such as meadow grass (blue grass, Poa), forage grass such as festuca, lolium, temperate grass, such as Agrostis, and cereals, e.g. wheat, oats, rye, barley, race, sorghum and maize (corn).

Examples of dicot plants are tobacco, legumes, such as lupins, potato, sugar beet, pea, bean and soybean, and cruciferous (family Brassicaceae), such as cauliflower, oil seed rape and the closely related model organism Arabidopsis thaliana.

Examples of plant parts are stem, callus, leaves, root, fruits, seeds, and tubers. In the present context, also specific plant tissues, such as chloroplast, apoplast, mitochondria, vacuole, peroxisomes and cytoplasm are considered to be a plant part. Furthermore, any plant cell, whatever the tissue origin, is considered to be a plant part.

Also included within the scope of the invention are the progeny of such plants, plant parts and plant cells.

The transgenic plant or plant cell expressing the enzyme of the invention may be constructed in accordance with methods known in the art. In short the plant or plant cell is constructed by incorporating one or more expression constructs encoding the enzyme of the invention into the plant host genome and propagating the resulting modified plant or plant cell into a transgenic plant or plant cell.

Conveniently, the expression construct is a DNA construct which comprises a gene encoding the enzyme of the invention in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, eg on the basis of when, where and how the enzyme is desired to be expressed. For instance, the expression of the gene encoding the enzyme of the invention may be constitutive or inducible, or may be developmental, stage or tissue specific, and the gene product may be targeted to a specific tissue or plant part such as seeds or leaves. Regulatory sequences are eg described by Tague et al, Plant, Phys., 86, 506, 1988.

For constitutive expression the 35S-CaMV promoter may be used (Franck et al., 1980. Cell 21: 285–294). Organ-specific promoters may eg be a promoter from storage sink tissues such as seeds, potato tubers, and fruits (Edwards & Coruzzi, 1990. Annu. Rev. Genet. 24: 275–303), or from metabolic sink tissues such as meristems (Ito et al., 1994. Plant Mol. Biol. 24: 863–878), a seed specific promoter such as the glutelin, prolamin, globulin or albumin promoter from rice (Wu et al., Plant and Cell Physiology Vol. 39, No. 8 pp. 885–889 (1998)), a *Vicia faba* promoter from the legumin B4 and the unknown seed protein gene from *Vicia faba* described by Conrad U. et al, Journal of Plant Physiology Vol. 152, No. 6 pp. 708-711 (1998), a promoter from a seed oil body protein (Chen et al., Plant and cell physiology vol. 39, No. 9 pp. 935–941 (1999), the storage protein napA promoter from Brassica napus, or any other seed specific promoter known in the art, eg as described in WO 91/14772. Furthermore, the promoter may be a leaf specific promoter such as the rbcs promoter from rice or tomato (Kyozuka et al., Plant Physiology Vol. 102, No. 3 pp. 991–1000 (1993), the chlorella virus adenine methyltransferase gene promoter (Mitra, A. and Higgins, DW, Plant Molecular Biology Vol. 26, No. 1 pp. 85–93 (1994), or the aldP gene promoter from rice (Kagaya et al., 5 Molecular and General Genetics Vol. 248, No. 6 pp. 668–674 (1995), or a wound inducible promoter such as the potato pin2 promoter (Xu et al, Plant Molecular Biology Vol. 22, No. 4 pp. 573–588 (1993).

A promoter enhancer element may be used to achieve higher expression of the enzyme in the plant. For instance, the promoter enhancer element may be an intron which is placed between the promoter and the nucleotide sequence encoding the enzyme. For instance, Xu et al. op cit disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including Agrobacterium-mediated transformation, virus-mediated transformation, micro injection, particle bombardment, biolistic transformation, and electroporation (Gasser et al, Science, 244, 1293; Potrykus, Bio/Techn. 8, 535, 1990; Shimamoto et al, Nature, 338, 274, 1989).

Presently, *Agrobacterium tumefaciens* mediated gene transfer is the method of choice for generating transgenic dicots (for review Hooykas & Schilperoort, 1992. Plant Mol. Biol. 19: 15–38), however it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992. Plant J. 2: 275–281; Shimamoto, 1994. Curr. Opin. Biotechnol. 5: 158–162; Vasil et al., 1992. Bio/Technology 10: 667–674). An alternative method for transformation of monocots is based on protoplast transformation as described by Omirulleh S, et al., Plant Molecular biology Vol. 21, No. 3 pp. 415–428 (1993).

Following transformation, the transformants having incorporated the expression construct are selected and regenerated into whole plants according to methods well-known in the art.

Enzyme Preparation

In the present context, the term "enzyme preparation" is intended to mean either be a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant pectin degrading enzyme, but which microorganism simultaneously produces other enzymes, e.g. other pectin degrading enzymes, proteases, or cellulases, being naturally occurring fermentation products of the microorganism, i.e. the enzyme complex conventionally produced by the corresponding naturally occurring microorganism.

The pectin degrading enzyme preparation of the invention may further comprise one or more enzymes selected from the group consisting of proteases, cellulases (endo-β-1,4-glucanases), β-glucanases (endo-β-1,3(4)-glucanases), lipases, cutinases, peroxidases, laccases, amylases, glucoamylases, pectinases, reductases, oxidases, phenoloxidases, ligninases, pullulanases, arabinanases, hemicellulases, mannanases, xyloglucanases, xylanases, pectin acetyl esterases, rhamnogalacturonan acetyl esterases, polygalacturonases, rhamnogalacturonases, galactanases, pectat lyases, pectin lyases, pectin methylesterases, cellobiohydrolases, transglutaminases; or mixtures thereof. In a preferred embodiment, one or more or all enzymes in the preparation is produced by using recombinant techniques, i.e. the enzyme(s) is/are monocomponent enzyme(s) which is/are mixed with the other enzyme(s) to form an enzyme preparation with the desired enzyme blend.

Immunological Cross-Reactivity

Polyclonal antibodies (which are monospecific for a given enzyme protein) to be used in determining immunological cross-reactivity may be prepared by use of a purified pectin degrading enzyme. More specifically, antiserum against the pectin degrading enzyme of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation ((NH$_4$)$_2$ SO$_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Use in the Detergent or Cleaning Industry

In further aspects, the present invention relates to a detergent composition comprising the pectin degrading enzyme or enzyme preparation of the invention, to a process for machine treatment of fabrics comprising treating fabric during a washing cycle of a machine washing process with a washing solution containing pectin degrading enzyme or enzyme preparation of the invention, and to cleaning compositions, including laundry, hard surface cleaner, personal cleansing and oral/dental compositions, comprising a pectin degrading enzyme or enzyme preparation of the invention providing superior cleaning performance, i.e. superior stain removal.

Without being bound to this theory, it is believed that the mannanase of the present invention is capable of effectively degrading or hydrolysing any soiling or spots containing galatomannans and, accordingly, of cleaning laundry comprising such soilings or spots.

The cleaning compositions of the invention must contain at least one additional detergent component. The precise nature of these additional components, and levels of incorporation thereof will depend on the physical form of the composition, and the nature of the cleaning operation for which it is to be used.

The cleaning compositions of the present invention preferably further comprise a detergent ingredient selected from a selected surfactant, another enzyme, a builder and/or a bleach system.

The cleaning compositions according to the invention can be liquid, paste, gels, bars, tablets, spray, foam, powder or granular. Granular compositions can also be in "compact" form and the liquid compositions can also be in a "concentrated" form.

The compositions of the invention may for example, be formulated as hand and machine dishwashing compositions, hand and machine laundry detergent compositions including laundry additive compositions and compositions suitable for use in the soaking and/or pretreatment of stained fabrics, rinse added fabric softener compositions, and compositions for use in general household hard surface cleaning operations. Compositions containing such carbohydrases can also be formulated as sanitization products, contact lens cleansers and health and beauty care products such as oral/dental care and personal cleaning compositions.

When formulated as compositions for use in manual dishwashing methods the compositions of the invention preferably contain a surfactant and preferably other detergent compounds selected from organic polymeric compounds, suds enhancing agents, group II metal ions, solvents, hydrotropes and additional enzymes.

When formulated as compositions suitable for use in a laundry machine washing method,. the compositions of the invention preferably contain both a surfactant and a builder compound and additionally one or more detergent components preferably selected from organic polymeric compounds, bleaching agents, additional enzymes, suds suppressors, dispersants, lime-soap soap dispersants, soil suspension and anti-redeposition agents and corrosion inhibitors. Laundry compositions can also contain softening agents, as additional detergent components. Such compositions containing carbohydrase can provide fabric cleaning, stain removal, whiteness maintenance, softening, colour appearance, dye transfer inhibition and sanitization when formulated as laundry detergent compositions.

The compositions of the invention can also be used as detergent additive products in solid or liquid form. Such additive products are intended to supplement or boost the performance of conventional detergent compositions and can be added at any stage of the cleaning process.

If needed the density of the laundry detergent compositions herein ranges from 400 to 1200 g/liter, preferably 500 to 950 g/liter of composition measured at 20° C.

The "compact" form of the compositions herein is best reflected by density and, in terms of composition, by the amount of inorganic filler salt; inorganic filler salts are conventional ingredients of detergent compositions in powder form; in conventional detergent compositions, the filler salts are present in substantial amounts, typically 17–35% by weight of the total composition. In the compact compositions, the filler salt is present in amounts not exceeding 15% of the total composition, preferably not exceeding 10%, most preferably not exceeding 5% by weight of the composition. The inorganic filler salts, such as meant in the present compositions are selected from the alkali and alkaline-earth-metal salts of sulphates and chlorides. A preferred filler salt is sodium sulphate.

Liquid detergent compositions according to the present invention can also be in a "concentrated form", in such case, the liquid detergent compositions according the present invention will contain a lower amount of water, compared to conventional liquid detergents. Typically the water content of the concentrated liquid detergent is preferably less than 40%, more preferably less than 30%, most preferably less than 20% by weight of the detergent composition.

Suitable specific detergent compounds for use herein are selected from the group consisting of the specific compounds as described in WO 97/01629 which is hereby incorporated by reference in its entirety.

Mannanase may be incorporated into the cleaning compositions in accordance with the invention preferably at a level of from 0.0001% to 2%, more preferably from 0.0005% to 0.5%, most preferred from 0.001% to 0.1% pure enzyme by weight of the composition.

The cellulases usable in the present invention include both bacterial or fungal cellulases. Preferably, they will have a pH optimum of between 5 and 12 and a specific activity above 50 CEVU/mg (Cellulose Viscosity Unit). Suitable cellulases are disclosed in U.S. Pat. No. 4,435,307, J61078384 and WO96/02653 which discloses fungal cellulase produced from *Humicola insolens,* Trichoderma, Thielavia and Sporotrichum, respectively. EP 739 982 describes cellulases isolated from novel Bacillus species. Suitable cellulases are also disclosed in GB-A-2075028; GB-A-2095275; DE-OS-22 47 832 and WO95/26398.

Examples of such cellulases are cellulases produced by a strain of Humicola insolens (Humicola grisea var. thermoidea), particularly the strain *Humicola insolens,* DSM 1800. Other suitable cellulases are cellulases originated from *Humicola insolens* having a molecular weight of about 50kD, an isoelectric point of 5.5 and containing 415 amino acids; and a 43kD endo-beta-1,4-glucanase derived from *Humicola insolens,* DSM 1800; a preferred cellulase has the amino acid sequence disclosed in PCT Patent Application No. WO 91/17243. Also suitable cellulases are the EGIII cellulases from *Trichoderma longibrachiatum* described in WO94/21801. Especially suitable cellulases are the cellulases having color care benefits. Examples of such cellulases are the cellulases described in WO96/29397, EP-A-0495257, WO 91/17243, WO91/17244 and WO91/21801. Other suitable cellulases for fabric care and/or cleaning properties are described in WO96/34092, WO96/17994 and WO95/24471.

Said cellulases are normally incorporated in the detergent composition at levels from 0.0001% to 2% of pure enzyme by weight of the detergent composition.

Preferred cellulases for the purpose of the present invention are alkaline cellulases, i.e. enzyme having at least 25%, more preferably at least 40% of their maximum activity at a pH ranging from 7 to 12. More preferred cellulases are enzymes having their maximum activity at a pH ranging from 7 to 12. A preferred alkaline cellulase is the cellulase sold under the tradename Carezyme® by Novo Nordisk A/S.

Amylases (α and/or β) can be included for removal of carbohydrate-based stains. WO94/02597, Novo Nordisk A/S published Feb. 3, 1994, describes cleaning compositions which incorporate mutant amylases. See also WO95/10603, Novo Nordisk A/S, published Apr. 20, 1995. Other amylases known for use in cleaning compositions include both α- and β-amylases. (α-Amylases are known in the art and include those disclosed in U.S. Pat. No. 5,003,257; EP 252,666; WO/91/00353; FR 2,676,456; EP 285,123; EP 525,610; EP 368,341; and British Patent specification no. 1,296,839 (Novo). Other suitable amylases are stability-enhanced amylases described in WO94/18314, published Aug. 18, 1994 and WO96/05295, Genencor, published Feb. 22, 1996 and amylase variants having additional modification in the immediate parent available from Novo Nordisk A/S, disclosed in WO 95/10603, published April 95. Also suitable are amylases described in EP 277 216, WO95/26397 and WO96/23873 (all by Novo Nordisk).

Examples of commercial α-amylases products are Purafect Ox Am® from Genencor and Termamyl®, Ban®, Fungamyl® and Duramyl®, all available from Novo Nordisk A/S Denmark. WO95/26397 describes other suitable amylases : α-amylases characterised by having a specific activity at least 25% higher than the specific activity of Termamyl® at a temperature range of 25° C. to 55° C. and at a pH value in the range of 8 to 10, measured by the Phadebas® ® α-amylase activity assay. Suitable are variants of the above enzymes, described in WO96/23873 (Novo Nordisk). Other amylolytic enzymes with improved properties with respect to the activity level and the combination of thermostability and a higher activity level are described in WO95/35382.

Preferred amylases for the purpose of the present invention are the amylases sold under the tradename Termamyl, Duramyl and Maxamyl and or the α-amylase variant demonstrating increased thermostability disclosed as SEQ ID No. 2 in WO96/23873.

Preferred amylases for specific applications are alkaline amylases, ie enzymes having an enzymatic activity of at least 10%, preferably at least 25%, more preferably at least 40% of their maximum activity at a pH ranging from 7 to 12. More preferred amylases are enzymes having their maximum activity at a pH ranging from 7 to 12.

The amylolytic enzymes are incorporated in the detergent compositions of the present invention a level of from 0.0001% to 2%, preferably from 0.00018% to 0.06%, more preferably from 0.00024% to 0.048% pure enzyme by weight of the composition.

The term xyloglucanase encompasses the family of enzymes described by Vincken and Voragen at Wageningen University [Vincken et al (1994) Plant Physiol., 104, 99–107] and are able to degrade xyloglucans as described in Hayashi et al (1989) Plant. Physiol. Plant Mol. Biol., 40, 139–168. Vincken et al demonstrated the removal of xyloglucan coating from cellulase of the isolated apple cell wall by a xyloglucanase purified from *Trichoderma viride* (endo-IV-glucanase). This enzyme enhances the enzymatic degradation of cell wall-embedded cellulose and work in synergy with pectic enzymes. Rapidase LIQ+ from Gist-Brocades contains an xyloglucanase activity.

This xyloglucanase is incorporated into the cleaning compositions in accordance with the invention preferably at a level of from 0.0001% to 2%, more preferably from 0.0005% to 0.5%, most preferred from 0.001% to 0.1 % pure enzyme by weight of the composition.

Preferred xyloglucanases for specific applications are alkaline xyloglucanases, ie enzymes having an enzymatic activity of at least 10%, preferably at least 25%, more preferably at least 40% of their maximum activity at a pH ranging from 7 to 12. More preferred xyloglucanases are enzymes having their maximum activity at a pH ranging from 7 to 12.

The above-mentioned enzymes may be of any suitable origin, such as vegetable, animal, bacterial, fungal and yeast origin. Origin can further be mesophilic or extremophilic (psychrophilic, psychrotrophic, thermophilic, barophilic, alkalophilic, acidophilic, halophilic, etc.). Purified or non-purified forms of these enzymes may be used. Nowadays, it is [co]mmon practice to modify wild-type enzymes via protein or genetic engineering techniques in order to optimise their performance efficiency in the cleaning compositions of the invention. For example, the variants may be designed such that the compatibility of the enzyme to commonly encountered ingredients of such compositions is increased. Alternatively, the variant may be designed such that the optimal pH, bleach or chelant stability, catalytic activity and the like, of the enzyme variant is tailored to suit the particular cleaning application.

In particular, attention should be focused on amino acids sensitive to oxidation in the case of bleach stability and on surface charges for the surfactant compatibility. The isoelectric point of such enzymes may be modified by the substitution of some charged amino acids, e.g. an increase in isoelectric point may help to improve compatibility with anionic surfactants. The stability of the enzymes may be further enhanced by the creation of e.g. additional salt bridges and enforcing metal binding sites to increase chelant stability.

Use in the Textile and Cellulosic Fiber Processing Industries

The pectin degrading enzyme of the present invention can be used alone or in combination with other carbohydrate degrading enzymes (for instance arabinanase, xyloglucanase, mannanase) for biopreparation of fibers or for cleaning of fibers in combination with detergents. Cotton fibers consist of a primary cell wall layer containing pectin and a secondary layer containing mainly cellulose. Under cotton preparation or cotton refining part of the primary cell wall will be removed. The present invention relates to either help during cotton refining by removal of the primary cell wall. Or during cleaning of the cotton to remove residual pectic substances and prevent graying of the textile.

In the present context, the term "cellulosic material" is intended to mean fibers, sewn and unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

The enzyme or preparation of the present invention is useful in the cellulosic fiber processing industry for the pretreatment or retting of fibers from hemp, flax or linen.

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types. Knitted goods are constructed by forming a network of interlocking loops from one continuous length of yarn. The cellulosic fibers can also be used for non-woven fabric.

The preparation process prepares the textile for the proper response in dyeing operations. The sub-steps involved in preparation are a. Desizing (for woven goods) using polymeric size like e.g. starch, CMC or PVA is added before weaving in order to increase the warp speed; This material must be removed before further processing.

b. Scouring, the aim of which is to remove non-cellulosic material from the cotton fiber, especially the cuticle (mainly consisting of waxes) and primary cell wall (mainly consisting of pectin, protein and xyloglucan). A proper wax removal is necessary for obtaining a high wettability, being a measure for obtaining a good dyeing. Removal of the primary cell wall—especially the pectins—improves wax removal and ensures a more even dyeing. Further this improves the whiteness in the bleaching process. The main chemical used in scouring is sodium hydroxide in high concentrations, up to 70 g/kg cotton and at high temperatures, 80–95° C.; and c. Bleaching; normally the scouring is followed by a bleach using hydrogen peroxide as the oxidizing agent in order to obtain either a fully bleached (white) fabric or to ensure a clean shade of the dye.

A one step combined scour/bleach process is also used by the industry. Although preparation processes are most commonly employed in the fabric state; scouring, bleaching and dyeing operations can also be done at the fiber or yarn stage.

The processing regime can be either batch or continuous with the fabric being contacted by the liquid processing stream in open width or rope form. Continuous operations generally use a saturator whereby an approximate equal weight of chemical bath per weight of fabric is applied to the fabric, followed by a heated dwell chamber where the chemical reaction takes place. A washing section then prepares the fabric for the next processing step. Batch processing generally takes place in one processing bath whereby the fabric is contacted with approximately 8–15 times its weight in chemical bath. After a reaction period, the chemicals are drained, fabric rinsed and the next chemical is applied. Discontinuous pad-batch processing involves a saturator whereby an approximate equal weight of chemical bath per weight of fabric is applied to the fabric, followed by a dwell period which in the case of cold pad-batch might be one or more days.

Woven goods are the prevalent form of textile fabric construction. The weaving process demands a "sizing" of the warp yarn to protect it from abrasion. Starch, polyvinyl alcohol (PVA), carboxymethyl cellulose, waxes and acrylic binders are examples of typical sizing chemicals used because of availability and cost. The size must be removed after the weaving process as the first step in preparing the woven goods. The sized fabric in either rope or open width form is brought in contact with the processing liquid containing the desizing agents. The desizing agent employed depends upon the type of size to be removed. For PVA sizes, hot water or oxidative processes are often used. The most common sizing agent for cotton fabric is based upon starch. Therefore most often, woven cotton fabrics are desized by a combination of hot water, the enzyme ($\alpha$-amylase to hydrolyze the starch and a wetting agent or surfactant. The cellulosic material is allowed to stand with the desizing chemicals for a "holding period" sufficiently long to accomplish the desizing. The holding period is dependent upon the type of processing regime and the temperature and can vary from 15 minutes to 2 hours, or in some cases, several days. Typically, the desizing chemicals are applied in a saturator bath which generally ranges from about 15° C. to about 55° C. The fabric is then held in equipment such as a "J-box" which provides sufficient heat, usually between about 55° C. and about 100° C., to enhance the activity of the desizing agents. The chemicals, including the removed sizing agents, are washed away from the fabric after the termination of the holding period.

In order to ensure a high whiteness or a good wettability and resulting dyeability, the size chemicals and other applied chemicals must be thoroughly removed. It is generally believed that an efficient desizing is of crucial importance to the following preparation processes: scouring and bleaching.

The scouring process removes much of the non-cellulosic is compounds naturally found in cotton. In addition to the natural non-cellulosic impurities, scouring can remove dirt, soils and residual manufacturing introduced materials such as spinning, coning or slashing lubricants. The scouring process employs sodium hydroxide or related causticizing agents such as sodium carbonate, potassium hydroxide or mixtures thereof. Generally an alkali stable surfactant is added to the process to enhance solubilization of hydrophobic compounds and/or prevent their redeposition back on the fabric. The treatment is generally at a high temperature, 80° C.–100° C., employing strongly alkaline solutions, pH 13–14, of the scouring agent. Due to the non-specific nature of chemical processes not only are the impurities but the cellulose itself is attacked, leading to damages in strength or other desirable fabric properties. The softness of the cellulosic fabric is a function of residual natural cotton waxes. The non-specific nature of the high temperature strongly alkaline scouring process cannot discriminate between the desirable natural cotton lubricants and the manufacturing introduced lubricants. Furthermore, the conventional scouring process can cause environmental problems due to the highly alkaline effluent from these processes. The scouring stage prepares the fabric for the optimal response in bleaching. An inadequately scoured fabric will need a higher level of bleach chemical in the subsequent bleaching stages.

The bleaching step decolorizes the natural cotton pigments and removes any residual natural woody cotton trash components not completely removed during ginning, carding or scouring. The main process in use today is an alkaline hydrogen peroxide bleach. In many cases, especially when a very high whiteness is not needed, bleaching can be combined with scouring.

In the examples below it is shown that the scouring step can be carried out using the pectate lyase or pectate lyase preparation of the present invention a temperature of about 50° C.–80° C. and a pH of about 7–11, thus substituting or supplementing the highly causticizing agents. An optimized enzymatic process ensures a high pectin removal and full wettability.

Degradation or Modification of Plant Material

The enzyme or enzyme preparation according to the invention is preferably used as an agent for degradation or modification of plant cell walls or any pectin-containing material originating from plant cells walls due to the high plant cell wall degrading activity of the enzyme of the invention.

The pectin degrading enzyme of the present invention may be used alone or together with other enzymes like glucanases, pectinases and/or hemicellulases to improve the extraction of oil from oil-rich plant material, like soy-bean oil from soy-beans, olive-oil from olives or rapeseed-oil from rape-seed or sunflower oil from sunflower.

The pectin degrading enzyme of the present invention may be used for separation of components of plant cell materials. Of particular interest is the separation of sugar or starch rich plant material into components of considerable commercial interest (like sucrose from sugar beet or starch from potato) and components of low interest (like pulp or hull fractions). Also, of particular interest is the separation of protein-rich or oil-rich crops into valuable protein and oil and invaluable hull fractions, The separation process may be performed by use of methods known in the art.

The pectin degrading enzyme of the invention may also be used in the preparation of fruit or vegetable juice in order to increase yield, and in the enzymatic hydrolysis of various plant cell wall-derived materials or waste materials, e.g. from wine or juice production, or agricultural residues such as vegetable. hulls, bean hulls, sugar beet pulp, olive pulp, potato pulp, and the like.

The plant material may be degraded in order to improve different kinds of processing, facilitate purification or extraction of other component than the galactans like purification of pectins from citrus,.improve the feed value, decrease the water binding capacity, improve the degradability in waste water plants, improve the conversion of plant material to ensilage, etc.

By means of an enzyme preparation of the invention it is possible to regulate the consistency and appearence of processed fruit or vegetables. The consistency and appearence has been shown to be a product of the actual combination of enzymes used for processing, i.e. the specificity of the enzymes with which the pectate lyase of the invention is combined. Examples include the production of clear juice e.g. from apples, pears or berries; cloud stable juice e.g. from apples, pears, berries, citrus or tomatoes; and purees e.g. from carrots and tomatoes.

The pectin degrading enzyme of the invention may be used in modifying the viscosity of plant cell wall derived material. For instance, the pectin degrading enzyme may be used to reduce the viscosity of feed which contain galactan and to promote processing of viscous galactan containing material. The viscosity reduction may be obtained by treating the galactan containing plant material with an enyme preparation of the invention under suitable conditions for full or partial degradation of the galactan containing material.

The pectin degrading enzyme can be used e.g. in combination with other enzymes for the removal of pectic substances from plant fibres. This removal is essential.e.g. in the production of textile fibres or other cellulosic materials. For this purpose plant fibre material is treated with a suitable amount of the pectin degrading enzyme of the invention under suitable conditions for obtaining full or partial degradation of pectic substances associated with the plant fibre material.

Animal Feed Additive

Pectin degrading enzyme of the present invention may be used for modification of animal feed and may exert their effect either in vitro (by modifying components of the feed) or in vivo. The pectin degrading enzyme is particularly suited for addition to animal feed compositions containing high amounts of arabinogalactans or galactans, e.g. feed containing plant material from soy bean, rape seed, lupin etc. When added to the feed the pectin degrading enzyme significantly improves the in vivo break-down of plant cell wall material, whereby a better utilization of the plant nutrients by the animal is achieved. Thereby, the growth rate and/or feed conversion ratio (i.e. the weight of ingested feed relative to weight gain) of the animal is improved. For example the indigestible galactan is degraded by pectate lyase, e.g. in combination with β-galactosidase, to galactose or galactooligomers which are digestible by the animal and thus contribute to the available energy of the feed. Also, by the degradation of galactan the pectate lyase may improve the digestibility and uptake of non-carbohydrate feed constituents such as protein, fat and minerals.

For further description reference is made to PCT/DK 96/00443 and a working example herein.

Wine and Juice Processing

The enzyme or enzyme preparation of the invention may be used for de-pectinization and viscosity reduction in vegetable or fruit juice, especially in apple or pear juice. This may be accomplished by treating the fruit or vegetable juice with an enzyme preparation of the invention in an amount effective for degrading pectin-containing material contained in the fruit or vegetable juice.

The enzyme or enzyme preparation may be used in the treatment of mash from fruits and vegetables in order to improve the extractability or degradability of the mash. For instance, the enzyme preparation may be used in the treatment of mash from apples and pears for juice production, and in the mash treatment of grapes for wine production.

Determination of Catalytic Activity of Pectin Degrading Enzymes

The Viscosity Assay APSU

APSU units: The APSU unit assay is a viscosity measurement using the substrate polygalacturonic acid with no added calcium.

The substrate 5% polygalacturonic acid sodium salt (Sigma P-1879) is solubilised in 0.1 M Glycin buffer pH 10. The 4 ml substrate is preincubated for 5 min at 40° C. The enzyme is added (in a volume of 250µl) and mixed for 10 sec on a mixer at maximum speed, it is then incubated for 20 min at 40° C. For a standard curve double determination of a dilution of enzyme concentration in the range of 5 APSU/ml to above 100 APSU/ml with minimum of 4 concentrations between 10 and 60 APSU per ml The viscosity is measured using a MIVI 600 from the company Sofraser, 45700 Villemandeur, France. The viscosity is measured as mV after 10 sec.

For calculation of APSU units a enzyme standard dilution as described above was used for obtaining a standard curve:

| APSU/ml | mV |
|---------|-----|
| 0.00 | 300 |
| 4.00 | 276 |
| 9.00 | 249 |
| 14.00 | 227 |
| 19.00 | 206 |
| 24.00 | 188 |
| 34.00 | 177 |
| 49.00 | 163 |
| 99.00 | 168 |

The GrafPad Prism program, using a non linear fit with a one phase exponential decay with a plateau, was used for calculations. The plateau plus span is the mV obtained without enzyme. The plateau is the mV of more than 100 APSU and the half reduction of viscosity in both examples was found to be 12 APSU units with a standard error of 1.5 APSU.

The Lyase Assay (at 235 mm)

For determination of the β-elimination an assay measuring the increase in absorbance at 235 nm was carried out using the substrate 0.1% polygalacturonic acid sodium salt (Sigma P-1879) solubilised in 0.1 M Glycin buffer pH 10. For calculation of the catalytic rate an increase of 5.2 Absorbency at 235 units per min corresponds to formation of 1 μmol of unsaturated product (Nasuna and Starr (1966) J. Biol. Chem. Vol 241 page 5298–5306; and Bartling, Wegener and Olsen (1995) Microbiology Vol 141 page 873–881).

Steady state condition using a 0.5 ml cuvette with a 1 cm light path on a HP diode array spectrophotometer in a temperature controlled cuvette holder with continuous measurement of the absorbency at 235 nm. For steady state a linear increase for at least 200 sec was used for calculation of the rate. It was used for converted to formation μmol per min product.

Agar Assay

Pectate lyase activity can be measured by applying a test solution to 4 mm holes punched out in agar plates (such as, for example, LB agar), containing 0.7% w/v sodium polygalacturonate (Sigma P 1879). The plates are then incubated for 6 h at a particular temperature (such as, e.g., 75° C.). The plates are then soaked in either (i) 1M CaCl2 for 0.5h or (ii) 1% mixed alkyl trimethylammonium Br (MTAB, Sigma M-7635) for 1 h. Both of these procedures cause the precipitation of polygalacturonate within the agar. Pectate lyase activity can be detected by the appearance of clear zones within a background of precipitated polygalacturonate. Sensitivity of the assay is calibrated using dilutions of a standard preparation of pectate lyase.

Endpoint Analysis—Transelimination at 235 nm for Pectate Lyases (High Calcium Method: 1 mM Calcium in the Final Incubation Mixture)

In this method, the substrate and enzyme is incubated for 20 min at 37° C. followed by measurement at 235 nm of the formation of double bounds. Finally, the rate of the degradation is calculated based on the molar extinction coefficient in terms of Trans Units.

Procedure:

Mixing of 0,5 ml enzyme dilution with 0,5 ml 2*substrate solution.

Substrate :Polygalactoronic acid from Sigma P-1879 lot 77H3784

Buffer 2x: 0.1M Glycin pH 10+2.0 mmol $CaCl_2$

Stop reagent: 0.02 M $H_3PO_4$

Temperature of incubation 37° C.

Reaction time 20 min.

Extinction coefficient of the transelimination 0.0052 μmol $cm^{-1}$

Enzyme diluted in ion-free water to 0.5 to 5 APSU per ml. Main value in duplicate 0.5 ml. The 2% w/v substrate in 2xbuffer is mixed with 0.5 ml diluted enzyme Both pre-incubated 5 min on water bath at –37° C. Incubate for 20 min. Stop using 5 ml stop reagent and mix. Blank mix enzyme and stop reagent first and then ad substrate all in the same volume.

| Enzyme | 0.5 ml |
|--------|--------|
| Substrate | 0.5 ml |
| Stop | 5 ml |
| Total volume | 6 ml |

Measure the absorbency at 235 nm in a 1 cm cuvette.

Calculate the formation of transelimination per min using the extinction coefficient of 0.0052 μmole cm–1

Calculation: [(main plus main)/2 -Blank] 0,0052*6*2*Enzyme dilution/20min/1000 ml=μmol per min.

Endpoint Analysis—Transelimination at 235 nm for Pectin Lyases at pH 9.0

The method is carried out as described above for the Endpoint analysis—Transelimination at 235 nm for Pectate Lyases (high Calcium method) but using the following substrate and buffer:

Substrate:Pectin Esterifired from Citrus from Sigma P-9561 lot 125HO123.

Buffer 2x: 0.1M Borate pH 9.0, SmM EDTA.

Materials and Methods

Strains

*Bacillus licheniformis* ATCC 14580.

*B. subtilis* PL2306. This strain is the *B. subtilis* DN1885 with disrupted apr and npr genes (Diderichsen, B., Wedsted, U., Hedegaard, L., Jensen, B. R., Sjøholm, C. (1990) Cloning of aldB, which encodes alpha-acetolactate decarboxylase, an exoenzyme from Bacillus brevis. J. Bacteriol., 172, 4315–4321) disrupted in the transcriptional unit of the known *Bacillus subtilis* cellulase gene, resulting in cellulase negative cells. The disruption was performed essentially as described in (. Eds. A. L. Sonenshein, J. A. Hoch and Richard Losick (1993) *Bacillus subtilis* and other Gram-Positive Bacteria, American Society for microbiology, p.618).

Competent cells were prepared and transformed as described by Yasbin, R. E., Wilson, G. A. and Young, F. E. (1975) Transformation and transfection in lysogenic strains of *Bacillus subtilis:* evidence for selective induction of prophage in competent cells. J. Bacteriol, 121:296–304.

Plasmids pMOL944

This plasmid is a pUB110 derivative essentially containing elements making the plasmid propagatable in *Bacillus subtilis,* kanamycin resistance gene and having a strong promoter and signal peptide cloned from the amyL gene of *B. licheniformis* ATCC14580. The signal peptide contains a SacII site making it convenient to clone the DNA encoding the mature part of a protein in-fusion with the signal peptide. This results in the expression of a Pre-protein which is directed towards the exterior of the cell.

The plasmid was constructed by means of conventional genetic engineering techniques which are briefly described in the following.

Construction of pMOL944

The pUB110 plasmid (McKenzie, T. et al., 1988, Plasmid 15:93–103) was digested with the unique restriction enzyme NciI. A PCR fragment amplified from the amyL promoter encoded on the plasmid pDN1981 (P. L. Jørgensen et al.,1990, Gene, 961. p37–41.) was digested with NciI and inserted in the NciI digested pUB110 to give the plasmid pSJ2624.

The two PCR primers used have the following sequences:
LWN5494
  5'-GTCGCCGGGGCGGCCGCTATCAAUrGGTAA CTGTATCTCAGC 3' (SEQ ID NO: 11)
LWN5495
  5-GTCGCCCGGGAGCTCTGATCAGGTACCMG CTTGTCGACCTGCAGAATG AGGCAGCAAGAAGAT-3' (SEQ ID NO: 12)

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:
LWN5938
  5'-GTCGGCGGCCGCTGATCACGTACCAAGCTT GTCGACCTGCAGMTG AOGCAGCAAGMGAT-3' (SEQ ID NO: 13)
LWN5939
  5'-GTCGGAGCTCTATCAATTGGTMCTGTATCTC AGC-3' (SEQ ID NO: 14)

The plasmid pSJ2670 was digested with the restriction enzymes PstI and BclII and a PCR fragment amplified from a cloned DNA sequence encoding the alkaline amylase SP722 (disclosed in the International Patent Application published as WO95/26397 which is hereby incorporated by reference in its entirety) was digested with PstI and BclII and inserted to give the plasmid pMOL944. The two primers used for PCR amplification have the following sequence:
LWN7864
  5'-AACAGCTGATCACGACTGATCTTTTAGCTT GGCAC-3' (SEQ ID NO: 15)
LWN7901
  5'-AACTGCAGCCGCGGCACATCATAATGGGAC AAATGGG-3' (SEQ ID NO: 16)

The primer #LWN7901 inserts a SacII site in the plasmid.

General Molecular Biology Methods

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers (e.g. restriction endonucleases, ligases etc. are obtainable from New England Biolabs, Inc.). TY (as described in Ausubel, F. M. et al. (eds.) "Current protocols in Molecular Biology". John Wiley and Sons, 1995). LB agar (as described in Ausubel, F. M. et al. (eds.) "Current protocols in Molecular Biology". John Wiley and Sons, 1995). LBPG is LB agar supplemented with 0.5% Glucose and 0.05 M potassium phosphate, pH 7.0 BPX media is described in EP 0 506 780 (WO 91/09129).

The following examples illustrate the invention.

EXAMPLE 1

Cloning, Expression, Purification and Characterization of a Pectate Lyase (II) from Bacillus licheniformis Genomic DNA Preparation Strain Bacillus licheniformis ATCC 14580 was propagated in liquid medium 3 as specified by ATCC (American Type Culture Collection, USA). After 18 hours incubation at 37° C. and 300 rpm, the cells were harvested, and genomic DNA isolated by the method described by Pitcher et al. (Pitcher, D. G., Saunders, N. A., Owen, R. J. (1989). Rapid extraction of bacterial genomic DNA with guanidium thiocyanate. Lett. Appl. Microbiol., 8, 151–156).

The pectate lyase II (vide supra, represented by amino acid sequence SEQ ID NO:8) encoding DNA sequence of the invention was PCR amplified using the PCR primer set consisting of these two oligo nucleotides:
PecI.B.Iich.upper.SacII
  5' CTA ACT GCA GCC GCO GCA GCT TCT GCC TTAAAC TCG GGC -3' (SEQ ID NO: 17)
PecI.B.Iich.Iower.NotI
  5' GCG TTG AGA CGC GCG GCC GCT GM TGC CCC GGA CGT TTC ACC-3' (SEQ ID NO: 18)

Restriction Sites SacII and NotII are Underlined.

Chromosomal DNA isolated from B. licheniformis ATCC 14580 as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM MgCl$_2$, 0.01% (w/v) gelatin) containing 200 $\mu$M of each dNTP, 2.5 units of AmpliTaq polymerase (Perkin-Elmer, Cetus, USA) and 100 pmol of each primer.

The PCR reactions was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-$\mu$l aliquots of the amplification product was analysed by electrophoresis in 0.7% agarose gels (NuSieve, FMC). The appearance of a DNA fragment size 1.0 kb indicated proper amplification of the gene segment.

Subcloning of PCR Fragment

Fortyfive-$\mu$l aliquots of the PCR products generated as described above were purified using QIAquick PCR purification kit (Qiagen, USA) according to the manufacturer's instructions. The purified DNA was eluted in 50 $\mu$l of 10 mM Tris-HCl, pH 8.5. 5 $\mu$g of pMOL944 and twentyfive-$\mu$l of the purified PCR fragment was digested with SacII and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 $\mu$g of each DNA fragment, 1 U of T4 DNA ligase and T4 ligase buffer (Boehringer Mannheim, Germany).

The ligation mixture was used to transform competent B. subtilis PL2306. The transformed cells were plated onto LBPG-10 $\mu$g/ml of Kanamycin plates. After 18 hours incubation at 37° C. several clones were restreaked on fresh agar plates and also grown in liquid TY cultures with 10 $\mu$g/ ml kanamycin and incubated overnight at 37° C. Next day 1 ml of cells were used to isolate plasmid from the cells using the Qiaprep Spin Plasmid Miniprep Kit #27106 according to the manufacturers recommendations for B. subtilis plasmid preparations. This plasmid DNA was used as template for DNA sequencing.

One clone containing the pectate lyase gene was kept, this clone was termed MB541.

The DNA corresponding to the mature part of the pectate lyase was characterised by DNA sequencing by primerwalking, using the Taq deoxy-terminal cycle sequencing kit (Perkin-Elmer, USA), fluorescent labelled terminators and appropriate oligonucleotides as primers.

Analysis of the sequence data was performed according to Devereux et al. (1984) Nucleic Acids Res. 12, 387–395. The cloned DNA sequence was expressed in B. subtilis and the protein that appeared in the supernatant corresponded to the mature protein represented in SEQ ID NO:8.

Purification

MB541 was grown in 25×200 ml BPX media with 10 μg/ml of Kanamycin in 500 ml two baffled shakeflasks for 5 days at 37° C. at 300 rpm, whereby 3500 ml of culture broth was obtained. The pH was adjusted to 5.0 using acetic acid and 100 ml of cationic agent (C521) and 200 ml of anionic agent (A130) was added during agitation for flocculation. The flocculated material was separated by centrifugation using a Sorval RC 3B centrifuge at 10000 rpm for 30 min at 6° C. The resulting supernatant contained 370 APSU per ml in a total volume of 3600 ml.

The supernatant was clarified using Whatman glass filters GF/D and C and finally concentrated on a filtron UF membrane with a cut off of 10 kDa. The total volume of 2000 ml was adjusted to pH 8.5. 50 gram of DEAE A-50 Sephadex (Pharmacia) was swelled in 2000 ml 50 mM Tris pH 8.5. Excess buffer was discarded and the clear concentrated enzyme solution was mixed with the slurry for 15 min. The enzyme was separated from the ion-exchange material by suction on a Buchner funnel. The resulting solution was concentrated on a filtron with a cut off of 10 kDa to a final volume of 800 ml.

For obtaining a highly purified pectate lyase a final step using S-sepharose cation-exchange chromatography was carried out. 50 ml of the solution of 950 APSU per ml (see above) was adjusted to pH 5.0 using acetic acid. It was applied to a 50 ml column containing S-Sepharose (Pharmacia) equilibrated with a buffer of 50 mmol sodium acetate pH 5.0. The pectate lyase bound and was eluted using a gradient of 0.5 M sodium chloride.

Characterisation

The pure enzyme gave a single band in SDS-PAGE of 35 kDa and an isoelectric point of around 6.1.

The protein concentration was determined using a molar extinction coefficient of 57750 (based on the amino acid composition deducted from the sequence).

Using the assay of detection the formation of cleavage by the formation of a double bound which can be measured at 235 nm the following data were obtained
1. (conditions: pH 10; glycine buffer; no calcium; polygalacturonic acid Sigma P-1879 as substrate): 1 μmol per min per mg.
2. (conditions: pH 10; glycine buffer; no calcium; DE 35 (35% esterified pectin) as substrate): 4 μmol per min per mg.

The pure enzyme was dialysed against EDTA at pH 8.0 (20 mM tris pH 8.0, and at pH 10 (20 mM Glycine pH 10) and the enzyme analysed in Circular dichroism, no differences was seen in the spectra with and with out EDTA.

Differential Scanning Calorimetry DSC of the 4 samples showed that the enzyme was most stable at pH 8.0 with a melting temperature around 70° C. in Tris pH 8.0 and 75° C. after dialysis against EDTA. At pH 10 the enzyme melted at 55° C. with and without EDTA.

The catalytic activity of the pectate lyase is inhibited by the presence of EDTA during incubation with substrate but the enzyme dialysed against EDTA was still active if EDTA was omitted during incubation with substrate. Divalent cation like Fe++, Li++, Mg++, Cu++, Mn++ has no effect on the catalytic activity.

The β-transelimination activity (using the lyase assay at 235 nm) at different pH values was determined as steady state kinetic at 40° C. using the following buffers:
pH 6.0: Na-MES 0.1M
pH 6.5, 7.0 & 7.5: Na-MOPS 0.1M
pH 8.0 & 8.5: Tris 0.1M
pH 9.0, 9.5, 10.0 & 10.5: Na-glycine 0.1M
pH: 11–11.5: Na-Carbonate 0.1M
MES: From SIGMA number M-8250 (2[N-Morpholino] ethane sulfonic acid).
MOPS: From SIGMA number M-1254 (3-[N-Morpholino] propane sulfonic acid).
TRIS: From Merck No. 1.08382
Glycine from MERCK and sodium carbonate from Merck No. 6392.

The relative activity (rate) is calculated as percentage of the optimum activity, the following result was obtained:

| pH | % activity |
| --- | --- |
| 6.5 | 1 |
| 7 | 5 |
| 7.5 | 4 |
| 8 | 4 |
| 8.5 | 4 |
| 9 | 6 |
| 9.5 | 23 |
| 10 | 100 |
| 10.5 | n.d. |
| 11 | 52 |
| 11.2 | 0 |

Correspondingly, the relative activity at different temperatures (at pH 10) was found:

| temp. ° C. | % activity |
| --- | --- |
| 40 | 65 |
| 50 | 87 |
| 55 | 87 |
| 60 | 100 |
| 65 | 90 |

Activity in detergents: Using commercial detergents instead of buffer and incubation for 20 min. at 40° C. with Polygalacturonic acid sodium salt (Sigma P-1879) followed by determination of the reducing sugars, the enzyme was active in European commercial powder detergent Ariel Futur with 44% relative activity, US Tide commercial powder with 51% relative activity and in US Tide commercial liquid detergent with 30% relative activity to the activity measured in Glycine buffer. The detergent concentration as the one recommended for use and the water tap water with 18 degree German hardness under European conditions and 9 degree under US conditions.

Immunological properties: At the Danish company DAKO, rabbit polyclonal monospecific serum was raised against the highly purified pectate lyase using conventional techniques. The serum formed a nice single precipitate in agarose gels with the pectate lyase of the invention and only one precipitation arch against Bacillus licheniformis crude products like Pulpzyme HC batch no. CKF0054 or batch no. CKN0009 from Novo Nordisk A/S.

EXAMPLE 2

Cloning, Expression, Purification and Characterization of a Pectate Lyase (I) from *Bacillus licheniformis*

Genomic DNA Preparation

The strain ATCC 14580 was propagated in liquid medium 3 as specified by ATCC (American Type Culture Collection, USA) After 18 hours incubation at 37° C. and 300 rpm, the cells were harvested, and genomic DNA was isolated by the method described in Pitcher et al. [Pitcher, D. G., Saunders, N. A., Owen, R. J; Rapid extraction of bacterial genomic DNA with guanidium thiocyanate; *Lett Appl Microbiol* 1989 8 151–156].

Definition of the Sequencee of the Invention

The sequence is defined by the following two primers which can be used in a subsequent PCR reaction for amplification of the entire open reading frame of the Pectate lyase of the invention:

PecI3.orf.PstI
5'-CAC ATC TGC AGC ATG MG AGA TTA GCA GGT ACG GTT ATT TTG TC-3' (SEQ ID NO 19)

PecI3.Licheniformis.lower.NotI
5-CTC ATC ATG CGG CCG CAG GGG CCT TTA TTT GCA ATC AGT G -3' (SEQ ID NO: 20).

Restriction Sites for Cloning Purposes are Underlined

The entire orf can be cloned using the above primers in a PCR carried out as described in example 1. The appearance of a DNA fragment size 0.7 kb indicates proper amplification of the gene segment. This DNA fragment can be cloned in any vector suitable for cloning in *E. coli*, *B. subtilis* or other. The fragment is cloned as a PstI-NotI fragment. When performing DNA sequencing on the PCR fragment or cloned fragment, the openreading frame of the DNA sequence thus appearing is shown in SEQ ID No. 3.

Subcloning and Expression of Pectate Lyase in *B. subtilis*

The Pectate lyase encoding DNA sequence (SEQ ID NO:3) of the invention was PCR amplified using the PCR primer set consisting of these two oligo nucleotides:

PecI3.Licheniformis.upper.PstI
5'-CAC ATC TGC AGO CGC GGC AGC CGA GGT CGT TCACAA AAC G -3' (SEQ ID NO: 21)

PecI3.Licheniformis.lower.NotI
5'- CTC ATC ATG CGG CO CAG GGG CCT TTA m GOCA ATC AGT G -3' (SEQ ID NO: 22)

Chromosomal DNA isolated from Bacillus licheniformis as described above was used as template in a PCR reaction carried out as described in example 1. The appearance of a DNA fragment size 0.6 kb indicated proper amplification of the gene segment.

Subcloning of PCR fragment was carried out as described in example 1 except that the purified PCR fragment was digested with PstI and NotI. Several clones were analysed by isolating plasmid DNA from overnight culture broth.

One such positive clone was restreaked several times on agar plates as used above, this clone was called MB750. The clone MB750 was grown overnight in TY-10 µg/ml kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations. This DNA was DNA sequenced and revealed the DNA sequence corresponding to the mature part of the Pectate lyase, i.e. positions 85–666 bp of the appended SEQ ID NO:3. The derived protein sequence is listed in SEQ.NO:4.

Fermentation and Purification

The clone MB 750 obtained as described above was grown in 200ml BPX media with 10 µg/ml of Kanamycin in 500 ml two baffled shakeflasks for 5 days at 37° C. at 300 rpm.

Flocculation was done using cationic flocculation agent C521 (10% solution) and 0.1% solution of anionic agent A130: To 1300 ml of fermentation medium at pH 6.0, 10 ml of C521 (10%) simultaneous with 20 ml of A130(0.1%) was added under stirring at room temperature. The flocculated material was separated by centrifugation using a Sorval RC 3B centrifuge at 10,000 rpm for 30 minutes. The liquid was concentrated into 200 ml using filtron ultrafiltration with a MW cut off of 10 kDa. This product was used for application trials after stabilization using 40% Glycerol (batch #9845 containing 193 Trans Units per ml or 1.97 mg active pectate lyase per ml).

Highly purified enzyme was obtained using Cationic chromatography S-Sepharose column at pH 5.5 using a 25 mM Sodium Acetate buffer) the enzyme eluted using a NaCl gradient, the final purification step was a size chromatography on a Superdex 200 column run in a 0.1 M Sodium acetate buffer.

Charaterisation

The pure enzyme has a MW of 22 kDa and a pI of 6.2.

The temperature optimum (relative activity) at pH 10 is 40° C.

The relative activity is higher than 50% between pH 9.5 and 10.5 at a temperataure of 40° C.

DSC of the enzyme at pH 6.0 gave a unfolding temperature of 61° C.

The N-terminal of the purified pectate lyase has the following sequence: AEVVHKTIV (starting at position 29 of the amino acid sequence SEQ ID NO:4).

This enzyme belongs to family 3 of polysaccharide lyases.

EXAMPLE 3

Cloning, Expression, Purification and Characterization of a Pectin Lyase (III) from *Bacillus licheniformis* Cloning of *Bacillus licheniformis* Pectin lyase Encoding Gene Subcloning and Expression of a *B. licheniformis* Pectin Lyase in *B. subtilis*

The Pectin lyase encoding DNA sequence SEQ ID no. .1 of the invention was PCR amplified using the PCR primer set consisting of the following two oligo nucleotides:

Pect.upper.PstI
5'-CAT AM TCT GCA GCC GCG GCA GCA MC GM GAT TAT CCG GAA C -3' (SEQ ID NO:23)

Pect.lower.NotI
5'-GAA AGS AAA AGC GGC CGC CAA ATA TTG AAA AGT GAG CGC AAT GTC G-3' (SEQ ID NO: 24)

Restriction sites PstI and NotI are underlined.

Chromosomal DNA isolated from *Bacillus licheniformis* as described above was used as template in a PCR reaction carried out as described in example 1. The appearance of a DNA fragment approximate size of 1.5 kb indicated proper amplification of the gene segment.

Subcloning of PCR Fragment

The subcloning was carried out as described in example 1 except that the purified PCR fragment was digested with PstI and NotI. Several clones were analyzed by isolating plasmid DNA from overnight culture broth.

One such positive clone was restreaked several times on agar plates as used above, this clone was called MB588. The clone MB588 was grown overnight in TY-10 µg/ml Kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations. This DNA was DNA sequenced and revealed the DNA sequence corresponding to the mature part of the Pectin lyase in the appended DNA sequence SEQ ID NO:1 and corresponding to the protein sequence in the appended protein sequence SEQ ID NO:2.

Fermentation and Purification

The clone MB588 obtained as described above was grown in 25×200 ml BPX media with 10 µg/ml of Kanamycin in 500 ml two baffled shakeflasks for 5 days at 37° C. at 300 rpm.

Flocculation was done using cationic flocculation agent 521 (10% solution) and 0.1% solution of anionic agent A130: To 2000 ml of fermentation medium pH 6.0 20 ml of C521 (10%) simultaneous with 40 ml of A130 was added under stirring at room temperature. The flocculated material was separated by centrifugation using a Sorval RC 3B centrifuge at 10,000 rpm for 30 minutes. The supernatant was clarified using Whatman glass filter number F.

The liquid was concentrated into 300 ml, using filtron ultrafiltration with a MW cut off of 10 kDa, containing 2,262,000 Trans Units on Pectin. The filtrate was adjusted to pH 5.5 using acetic acid and applied to S-Sepharose column equilibrated with 50 mM Sodium acetate pH 5.5. The pectin lyase bound and was eluted as a pure protein using a NaCl gradient.

Characterisation

The pure enzyme has a MW of 55 kDa and a pI of 9.3.

The relative activity is higher than 50% between pH 8.5 and 9.3 at a temperature of 40° C. (pectin is not stable esterified above 9.3).

This enzyme belongs to family 1 of polysaccharide lyases.

EXAMPLE 4

Construction and Expression of Fusion Protein Between Pectate Lyase and CBD

The CBD encoding DNA sequence of the CipB gene from *Clostridium thermocellum* strain YS (Poole D M; Morag E; Lamed R; Bayer E A; Hazlewood G P; Gilbert H J (1992) Identification of the cellulose-binding domain of the cellulosome subunit S1 from Clostridium thermocellum YS, Fems Microbiology Letters Vol. 78 No. 2–3 pp. 181–186 was PCR amplified using the PCR primer set consisting of the following two oligo nucleotides:

CIPCBD.upper.PECL.SalI
5'-CGA CAA TGT CGA TGT AAA ATC AAT CGT CAA GCA AAA TGC CGG AGT CGG CAA AAT CCA GCG CAG ACC GCC AAC ACC GAC CCC GAC CCC ACC GCC AAG CGC AAA TAC ACC GGT ATC AGG CAA TTT G-3' (SEQ ID NO: 25)

CIPCBD.lower.NotI
5'GCG TTG AGA CGC GCG GCC GCT ATA CCA CAC TGC CAC CGG GTT CTT TAC-3' (SEQ ID NO 26)

Restriction sites SalI and NotI are underlined.

Chromosomal DNA encoding the CBD can be obtained as described in Poole D M; Morag E; Lamed R; Bayer E A; Hazlewood G P Gilbert H J (1992) Identification of the cellulose-binding domain of the cellulosome subunit S1 from Clostridium thermocellum YS, Fems Microbiology Letters Vol. 78 , No. 2–3 pp. 181–186. A DNA sample encoding the CBD was used as template in a PCR reaction carried out as described in example 1. The appearance of a DNA fragment approximate size of 0.5 kb indicated proper amplification of the gene segment.

Subcloning of PCR Fragment

The subcloning was carried out as described in example 1 except that the purified PCR fragment was digested with SalI and NotI. Several clones were analyzed by isolating plasmid DNA from overnight culture broth.

One such positive clone was restreaked several times on agar plates as used above, this clone was called MB914. The clone MB914 was grown overnight in TY-10 µg/ml Kanamycin at 370C, and next day 1 ml of cells were used to isolate plasmid from the cells using the Qiaprep Spin Plasmid Miniprep Kit #27106 according to the manufacturers recommendations for *B. subtilis* plasmid preparations. This DNA was DNA sequenced and revealed the DNA sequence corresponding to the fusionprotein of: Pectate lyase-linker-cbd as represented in SEQ ID NO:9 and in the appended protein sequence SEQ ID NO:10.

Expression and Detection of Pectate-lyase-cbd Fusion Protein

MB914 was incubated for 20 hours in TY-medium at 37° C. and 250 rpm. 1 ml of cell-free supernatant was mixed with 200 µl of 10% Avicel (Merck, Darmstadt, Germany) in Millipore H2O. The mixture was left for ½ hour incubation at 0° C. After this binding of Pectatelyase-Linker-CBD fusion protein to Avicel the Avicel with bound protein was spun 5 min at 5000 g. The pellet was resuspended in 100 µl of SDS-page buffer, boiled at 95° C. for 5 min, spun at 5000 g for 5 min and 25 µl was loaded on a 4–20% Laemmli Tris-Glycine, SDS-PAGE NOVEX gel (Novex, USA). The samples were electrophoresed in a Xcell™ Mini-Cell (NOVEX, USA) as recommended by the manufacturer, all subsequent handling of gels including staining with comassie, destaining and drying were performed as described by the manufacturer.

The appearance of a protein band of approx. 55 kDa, indicated expression in *B.subtilis* of the Pectatelyase-Linker-CBD fusion encoded on the plasmid pMB914.

EXAMPLE 5

Pectate Lyase Treatment of Cellulosic Material

Effect of Temperature on Pectin Removal and Wettability

A 100% cotton woven twill fabric, desized Test Fabric #428U, representing a typical cellulosic material, was treated with an aqueous enzyme solution comprising the *B. licheniformis* pectate lyase of example 1, dosed at 9 APSU/g fabric at pH 9 and at a 15:1 liquor ratio. Treatment time was 2 hours and temperature varied between 35–75° C. The fabric was rinsed well after the enzyme treatment, dried and then dyed with Ruthenium Red. The dye uptake was measured spectrophotometrically and is a measure of the residual pectin on the fiber. The percentage of residual pectin was calculated using the dye uptake of the starting material as 100% residual pectin and that of fully chemically scoured and bleached fabric as 0%. Results are shown in Table 6. Further, the wettability (drop test—measuring the time in seconds for a drop of water to become absorbed by the fabric) was measured and compared to a no enzyme control. Results are shown in Table 7.

TABLE 6

| Temp., ° C. | (% residual pectin) | | | | |
| --- | --- | --- | --- | --- | --- |
| | 35 | 45 | 55 | 65 | 75 |
| no enzyme | 100 | 100 | 93 | 90 | 85 |
| enzyme | 52 | 40 | 32 | 28 | 26 |

- an alkaline scouring leaves typically 20–25% residual pectin

TABLE 7

| Temp., °C. | 35 | 45 | 55 | 65 | 75 |
|---|---|---|---|---|---|
| no enzyme | 32 | 29 | 29 | 12 | 11 |
| enzyme | 15 | 10 | 7 | 5 | 3 |

- wettability target is typically > 5 seconds

The beneficial effect of increasing temperature is clearly seen on both responses.

EXAMPLE 6
Pectate Lyase Treatment of Cellulosic Material
Effect of pH on Pectin Removal A 100% cotton woven twill fabric, desized Test Fabric #428U, representing a typical cellulosic material, was treated with an aqueous enzyme solution comprising the *B. licheniformis* pectate lyase of example 1, dosed at 9 APSU/g fabric at a 15:1 liquor ratio. Treatment time was 2 hours and the temperature 55° C. pH was varied between 8–11. The fabric was rinsed well after the enzyme treatment, dried and then dyed with Ruthenium Red. The dye uptake is measured spectrophotometrically and is a measure of the residual pectin on the fiber. The percentage of residual pectin was calculated using the dye uptake of the starting material as 100% residual pectin and that of fully chemically scoured and bleached fabric as 0%. The results are shown in Table 8:

TABLE 8

| pH | 8 | 9 | 10 | 10.5 | 11 |
|---|---|---|---|---|---|
| % residual pectin | 35 | 32 | 30 | 48 | 61 |

The pH optixnum is found to be at app. 9.5, but a good activity is demonstrated in a very broad alkaline interval.

EXAMPLE 7
Use of the Enzyme of the Invention in Detergents

The purified enzyme obtained as described in example 1 (batch 9751) showed improved cleaning performance when tested at a level of 1 ppm in a miniwash test using a conventional commercial liquid detergent. The test was carried out under conventional North American wash conditions.

EXAMPLE 8
Effects of Carbohydrases on Banana Stained Cotton Textile
Method

Three bananas were mashed and homogenised in a Ultra Turrax with 40 ml of water. Style 400 cotton (Testfabrics, Inc.) was soaked in the solution, squeezed between two rolls and dried overnight.

The stained cotton textile was washed in the commercial liquid detergent brand Ariel Futur Liquid under European wash conditions, with an addition of 0.1 ppm, 0.2 ppm, 1 ppm and 10 ppm, respectively, of the pectate lyase of example 1 to the detergent liquid. The test was repeated.
Results Ariel liquid: % removal of the banana stains (100% is total removal of stain)

|  | Test A | Test B |
|---|---|---|
| No enzyme | 26% | 32% |
| 10 ppm enzyme, ex 1 | 59% | 58% |
| 1 ppm enzyme, ex 1 | 47% | 48% |
| 0.1 ppm enzyme, exl | 35% | 34% |

LITERATURE

Lever, M. (1972) A new reaction for colormetric determination of carbohydrates. Anal. Biochem. 47, 273–279.

N. C. Carpita and D. M. Gibeaut (1993) The Plant Journal 3:1–30.

Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol. 172:4315–4321.

Sakai et al., Pectin, pectinase and protopectinase: production, properties and applications, pp 213–294 in: Advances in Applied Microbiology vol:39,1993.

What is claimed is:

1. An isolated polynucleotide molecule encoding a polypeptide having pectate lyase activity selected from the group consisting of:
   (a) polynucleotide molecules comprising a nucleotide sequence of nucleotides 82–1026 of SEQ ID NO: 7;
   (b) polynucleotide molecules that encode a polypeptide that is at least 90% identical to the amino acid sequence of residues 28–341 of SEQ ID NO: 8;
   (c) polynucleotide molecules that hybridize with the nucleotide sequence of SEQ ID NO:7 under hybridization conditions comprising 5×SSC at 45° C. and washing conditions comprising 2×SSC at 60° C.; and
   (d) degenerate nucleotide sequences of (a), (b) or (c).

2. The polynucleotide molecule of claim 1, wherein the polynucleotide is DNA.

3. A polynucleotide molecule of claim 1, which comprises a nucleotide sequence of nucleotides 82–1026 of SEQ ID NO: 7.

4. A polynucleotide molecule of claim 1, which is a polynucleotide molecule that encodes a polypeptide that is at least 90% identical to the amino acid sequence of residues 28–341 of SEQ ID NO: 8.

5. A polynucleotide molecule of claim 1, which hybridizes with the nucleotide sequence of SEQ ID NO:7 under hybridization conditions comprising 5×SSC at 45° C. and washing conditions comprising 2×SSC at 60° C.

6. An expression vector comprising the following operably linked elements: a transcription promoter; a polynucleotide molecule of claim 1 and a transcription terminator.

7. A cell comprising an expression vector of claim 6.

8. A method of producing a polypeptide having pectin degrading activity, comprising
   (a) culturing a cell of claim 7; and
   (b) recovering the polypeptide.

* * * * *